United States Patent [19]
Steffens

[11] Patent Number: 6,160,204
[45] Date of Patent: Dec. 12, 2000

[54] POLYPHENOL OXIDASE CDNA

[75] Inventor: John C. Steffens, Ithaca, N.Y.

[73] Assignee: Cornell Research Foundation, Inc., Ithaca, N.Y.

[21] Appl. No.: 08/481,190

[22] Filed: Jun. 7, 1995

Related U.S. Application Data

[63] Continuation of application No. 08/203,533, Feb. 28, 1994, abandoned, which is a continuation-in-part of application No. 07/833,839, Jan. 31, 1992, abandoned.

[51] Int. Cl.$^7$ .............................. A01H 5/00; C12N 15/82; C12N 5/04
[52] U.S. Cl. .................. 800/284; 800/286; 800/298; 800/317.2; 800/317.3; 800/317.4; 435/419; 435/468; 435/252.2; 435/252.3; 536/23.6
[58] Field of Search .................................. 800/205, 284, 800/286, 298, 317.2, 317.3, 317.4; 536/23.6; 435/69.1, 172.3, 240.4, 240.49, 320.1, 419, 468, 252.2, 252.3

[56] References Cited

U.S. PATENT DOCUMENTS

| | | | |
|---|---|---|---|
| 4,394,443 | 7/1983 | Weissman et al. | 435/6 |
| 4,525,368 | 6/1985 | Bengtsson et al. | 426/438 |
| 4,723,052 | 2/1988 | Cochran | 800/200 |
| 4,801,540 | 1/1989 | Hiatt | 435/172.3 |
| 4,814,192 | 3/1989 | Sapers et al. | 426/268 |
| 4,975,293 | 12/1990 | Hicks et al. | 426/271 |
| 4,981,708 | 1/1991 | McEvily | 426/262 |
| 5,059,438 | 10/1991 | McEvily et al. | 426/268 |

FOREIGN PATENT DOCUMENTS

WO 93/02195 2/1993 WIPO.
WO 94/03607 2/1994 WIPO.

OTHER PUBLICATIONS

Fischhoff et al (1987) Bio/Technology 5:807–813.
Rosahl et al (1986) Mol Gen Ganet 202:368–373.
Jacobs et al (1985) Nature 313:806–810.
Matsudaira (1987) J. Biol Chem 262 (21):10035–10038.
Matsudaira (1990) Methods in Enzymol 182:602–613.
Leonard et al (1984) Nature 311:626–631.
Larkins et al (1985) J. Cell Biochem Suppl O (9 part C):264.
Weising, K. et al., Annu Rev Genet 22:421–477 (1988).
Delauney, A.J. et al., Proc Natl Acad Sci USA 85:4300–4304 (1988).
Matsudaira, P., Methods in Enzymology 182:602–613 (1990).
Leonard, W.J., et al., Nature 311:626–631 (1984).
Larkins, B.A. et al., J. Cell Biochem Suppl. 0 (9 part C):264 (1985).
Fischhoff, D.A. et al., Bio/Technology 5:807–813 (1987).
Rosahl, S. et al., Mol Gen Genet 202:368–373 (1986).
Jacobs, K. et al., Nature 313:806–810 (1985).
Matsudaira, P., J Biol Chem 262(21):10035–10038 (1987).
Fils, B. et al., Sciences Des Aliments 5:217–232 (1985).
Batistuti, J.P. et al., Food Chemistry 18:251–263 (1985).
Gaser, C.S. et al., Science 244:1293–1299 (1989).
Mayer, A.M., Phytochemistry 26(1):11–20 (1987).
Mayer, A.M. and Harel, E., Phytochemistry 18:193–215 (1979).

*Primary Examiner*—Elizabeth F. McElwain
*Attorney, Agent, or Firm*—Nixon Peabody LLP

[57] ABSTRACT

The present invention describes the cloning and sequencing of plant Polyphenol Oxidase (PPO) cDNAs which has subsequently permitted their use to genetically transform plants to achieve a variety of desired phenotypes.

51 Claims, No Drawings

```
                         SEQUENCE LISTING (1) GENERAL INFORMATION:

(iii) NUMBER OF SEQUENCES:       19

(2) INFORMATION FOR SEQ ID NO:1:

(i) SEQUENCE CHARACTERISTICS:
         (A) LENGTH:      1761 base pairs
         (B) TYPE:                 nucleic acid
         (C) STRANDEDNESS:         single
         (D) TOPOLOGY:    linear (ii) MOLECULE TYPE:     cDNA (xi) SEQUENCE DESCRIPTION: SEQ ID NO:1:

ATG TCT TCT TCT TCT TCT ATT ACT ACT ACT CTT CCT TTA                39

TGC ACC AAC AAA TCC CTC TCT TCT TCC TTC ACC ACC ACC                78

AAC TCA TCC TTG TTA TCA AAA CCC TCT CAA CTT TTC CTC                117

CAC GGA AGG CGT AAT CAA AGT TTC AAG GTT TCA TGC AAC                156

GCA AAC AAC GTT GAC AAA AAC CCT GAC GCT GTT GAT AGA                195
```

```
CGA AAC GTT CTT TTA GGG TTA GGA GGT CTT TAT GGT GCA        234

GCT AAT CTT GCA CCA TTA GCG ACT GCT GCA CCT ATA CCA        273

CCT CCT GAT CTC AAG TCT TGT GGT ACT GCC CAT GTA AAA        312

GAA GGT GTT GAT GTA ATA TAC AGT TGT TGC CCT CCT GTA        351

CCC GAT GAG ATC GAT AGT GTT CCG TAC TAC AAG TTC CCT        390

TCT ATG ACT AAA CTC CGC ATC CGC CCC CCT GCT CAT GCG        429

GCG GAT GAG GAG TAC GTA GCC AAG TAT CAA TTG GCT ACG        468

AGT CGA ATG AGG GAA CTT GAT AAA GAC CCC TTT GAC CCT        507

CTT GGC TTT AAA CAA CAA GCT AAT ATT CAT TGT GCT TAT        546

TGC AAC GGT GCT TAC AAA GTT GGT GGT AAA GAA TTG CAA        585

GTT CAT TTC TCG TGG CTT TTC TTT CCC TTT CAT AGA TGG        624

TAC TTG TAC TTT TAC GAA AGA ATT TTG GGA TCA CTT ATT        663

AAT GAT CCA ACT TTT GCT TTA CCT TAC TGG AAT TGG GAT        702

CAT CCA AAA GGC ATG CGT ATA CCT CCC ATG TTT GAT CGT        741

GAG GGA TCA TCT CTT TAC GAT GAG AAA CGT AAC CAA AAT        780

CAT CGC AAT GGA ACT ATT ATT GAT CTT GGT CAT TTT GGT        819

AAG GAA GTT GAC ACA CCT CAG CTA CAG ATA ATG ACT AAT        858

AAT TTA ACC CTA ATG TAC CGT CAA ATG GTT ACT AAT GCT        897

CCT TGC CCT TCC CAA TTC TTC GGT GCT GCT TAC CCT CTG        936

GGT TCT GAA CCA AGT CCG GGT CAG GGT ACT ATT GAA AAC        975

ATC CCT CAT ACT CCG GTT CAC ATC TGG ACC GGT GAC AAA       1014

CCT CGT CAA AAA AAC GGT GAA GAC ATG GGT AAT TTC TAC       1053

TCA CCC GGT TTA GAT CCG ATT TTT TAC TGC CAC CAT GCC       1092

AAT GTG GAC AGG ATG TGG AAT GAA TGG AAA TTA ATT GGC       1131

GGG AAA AGA AGG GAT TTA ACA GAT AAA GAT TGG TTG AAC       1170

TCT GAA TTC TTT TTC TAC GAT GAA AAT CGT AAC CCT TAC       1209

CGT GTG AAG TCC GTA GAC TGT TTG GAC AGT AAA AAA ATG       1248

GGA TTC GAT TAC GCG CCA ATG CCC ACT CCA TGG CGT AAT       1287

TTT AAA CCA ATC AGA AAG TCA TCA TCA GGA AAA GTG AAT       1326

ACA GCG TCA ATT GCA CCA GTT AGC AAG GTG TTC CCA TTG       1365

GCG AAG CTG GAC CGT GCG ATT TCG TTC TCT ATC ACG CGG       1404

CCA GCC TCG TCA AGG ACA ACA CAA GAG AAA AAT GAG CAA       1443

GAG GAG ATA CTG ACA TTC AAT AAA ATA TCG TAT GAT GAT       1482

AGG AAC TAT GTA AGG TTC GAT GTG TTT CTG AAC GTG GAC       1521

AAG ACT GTG AAT GCA GAT GAG CTT GAT AAG GCG GAG TTT       1560

GCA GGG AGT TAT ACT AGC TTG CCG CAT GTT CAT GGA AGT       1599

AAT ACT AAT CAT GTT ACC AGT GTT ACT TTC AAG CTG GCG       1638

ATA ACT GAA CTG TTG GAG GAT ATT GGA TTG GAA GAT GAA       1677

GAT ACT ATT GCG GTG ACT TTG GTT CCA AAA GCT GGC GGT       1716

GAA GAA GTG TCC ATT GAA AGT GTG GAG ATC AAG CTT GAG       1755
```

```
GAT TGT                                                              1761

(2) INFORMATION FOR SEQ ID NO:2:

(i) SEQUENCE CHARACTERISTICS:
        (A) LENGTH:        30 base pairs
        (B) TYPE:          nucleic acid
        (C) STRANDEDNESS:  single
        (D) TOPOLOGY:      linear (ii) MOLECULE TYPE:    cDNA (xi) SEQUENCE DESCRIPTION: SEQ ID NO:2:

GGAATTCGGC ACGAGCTCCA TCACAACACA                                       30

(2) INFORMATION FOR SEQ ID NO:3:

(i) SEQUENCE CHARACTERISTICS:
        (A) LENGTH:        141 base pairs
        (B) TYPE:          nucleic acid
        (C) STRANDEDNESS:  single
        (D) TOPOLOGY:      linear (ii) MOLECULE TYPE:    cDNA (xi) SEQUENCE DESCRIPTION: SEQ ID NO:3:

TAAAGTCTGC ATGAGTTGGT GGCTATGGTG CCAAATTTTA TGTTTAATTA                  50

GTATAATTAT GTGTGGTTTG AGTTATGTTT TATGTTAAAA TGTATCAGCT                 100

CGATCGATAG CTGATTGCTA GTTGTGTTAA TGCTATGTAT G                          141

(2) INFORMATION FOR SEQ ID NO:4:

(i) SEQUENCE CHARACTERISTICS:
        (A) LENGTH:        587 amino acids
        (B) TYPE:          amino acid
        (C) STRANDEDNESS:  single
        (D) TOPOLOGY:      linear (ii) MOLECULE TYPE:    peptide (xi) SEQUENCE DESCRIPTION: SEQ ID NO:4:

Met Ser Ser Ser Ser Ser Ile Thr Thr Thr Leu Pro Leu Cys Thr
                5                  10                  15

Asn Lys Ser Leu Ser Ser Ser Phe Thr Thr Thr Asn Ser Ser Leu
            20                  25                  30

Leu Ser Lys Pro Ser Gln Leu Phe Leu His Gly Arg Arg Asn Gln
            35                  40                  45

Ser Phe Lys Val Ser Cys Asn Ala Asn Asn Val Asp Lys Asn Pro
            50                  55                  60

Asp Ala Val Asp Arg Arg Asn Val Leu Leu Gly Leu Gly Gly Leu
            65                  70                  75

Tyr Gly Ala Ala Asn Leu Ala Pro Leu Ala Thr Ala Ala Pro Ile
            80                  85                  90

Pro Pro Pro Asp Leu Lys Ser Cys Gly Thr Ala His Val Lys Glu
            95                 100                 105

Gly Val Asp Val Ile Tyr Ser Cys Cys Pro Pro Val Pro Asp Glu
           110                 115                 120

Ile Asp Ser Val Pro Tyr Tyr Lys Phe Pro Ser Met Thr Lys Leu
           125                 130                 135

Arg Ile Arg Pro Pro Ala His Ala Ala Asp Glu Glu Tyr Val Ala
           140                 145                 150
```

-continued

```
Lys Tyr Gln Leu Ala Thr Ser Arg Met Arg Glu Leu Asp Lys Asp
                155                 160                 165

Pro Phe Asp Pro Leu Gly Phe Lys Gln Gln Ala Asn Ile His Cys
                170                 175                 180

Ala Tyr Cys Asn Gly Ala Tyr Lys Val Gly Gly Lys Glu Leu Gln
                185                 190                 195

Val His Phe Ser Trp Leu Phe Phe Pro Phe His Arg Trp Tyr Leu
                200                 205                 210

Tyr Phe Tyr Glu Arg Ile Leu Gly Ser Leu Ile Asn Asp Pro Thr
                215                 220                 225

Phe Ala Leu Pro Tyr Trp Asn Trp Asp His Pro Lys Gly Met Arg
                230                 235                 240

Ile Pro Pro Met Phe Asp Arg Glu Gly Ser Ser Leu Tyr Asp Glu
                245                 250                 255

Lys Arg Asn Gln Asn His Arg Asn Gly Thr Ile Ile Asp Leu Gly
                260                 265                 270

His Phe Gly Lys Glu Val Asp Thr Pro Gln Leu Gln Ile Met Thr
                275                 280                 285

Asn Asn Leu Thr Leu Met Tyr Arg Gln Met Val Thr Asn Ala Pro
                290                 295                 300

Cys Pro Ser Gln Phe Phe Gly Ala Ala Tyr Pro Leu Gly Ser Glu
                305                 310                 315

Pro Ser Pro Gly Gln Gly Thr Ile Glu Asn Ile Pro His Thr Pro
                320                 325                 330

Val His Ile Trp Thr Gly Asp Lys Pro Arg Gln Lys Asn Gly Glu
                335                 340                 345

Asp Met Gly Asn Phe Tyr Ser Pro Gly Leu Asp Pro Ile Phe Tyr
                350                 355                 360

Cys His His Ala Asn Val Asp Arg Met Trp Asn Glu Trp Lys Leu
                365                 370                 375

Ile Gly Gly Lys Arg Arg Asp Leu Thr Asp Lys Asp Trp Leu Asn
                380                 385                 390

Ser Glu Phe Phe Phe Tyr Asp Glu Asn Arg Asn Pro Tyr Arg Val
                395                 400                 405

Lys Ser Val Asp Cys Leu Asp Ser Lys Lys Met Gly Phe Asp Tyr
                410                 415                 420

Ala Pro Met Pro Thr Pro Trp Arg Asn Phe Lys Pro Ile Arg Lys
                425                 430                 435

Ser Ser Ser Gly Lys Val Asn Thr Ala Ser Ile Ala Pro Val Ser
                440                 445                 450

Lys Val Phe Pro Leu Ala Lys Leu Asp Arg Ala Ile Ser Phe Ser
                455                 460                 465

Ile Thr Arg Pro Ala Ser Ser Arg Thr Thr Gln Glu Lys Asn Glu
                470                 475                 480

Gln Glu Glu Ile Leu Thr Phe Asn Lys Ile Ser Tyr Asp Asp Arg
                485                 490                 495

Asn Tyr Val Arg Phe Asp Val Phe Leu Asn Val Asp Lys Thr Val
                500                 505                 510

Asn Ala Asp Glu Leu Asp Lys Ala Glu Phe Ala Gly Ser Tyr Thr
                515                 520                 525

Ser Leu Pro His Val His Gly Ser Asn Thr Asn His Val Thr Ser
                530                 535                 540
```

-continued

```
Val Thr Phe Lys Leu Ala Ile Thr Glu Leu Leu Glu Asp Ile Gly
                545                 550                 555

Leu Glu Asp Glu Asp Thr Ile Ala Val Thr Leu Val Pro Lys Ala
                560                 565                 570

Gly Gly Glu Glu Val Ser Ile Glu Ser Val Glu Ile Lys Leu Glu
                575                 580                 585

Asp Cys
    587
```

(2) INFORMATION FOR SEQ ID NO:5:

(i) SEQUENCE CHARACTERISTICS:
        (A) LENGTH:    1788 base pairs
        (B) TYPE:         nucleic acid
        (C) STRANDEDNESS:    single
        (D) TOPOLOGY:    linear (ii) MOLECULE TYPE:    cDNA (xi) SEQUENCE DESCRIPTION: SEQ ID NO:5:

```
ATG GCA AGT GTA GTG TGC AAT AGT AGT AGT AGT ACT ACT              39

ACT ACA ACG CTC AAA ACT CCT TTT ACT TCT TTA GGT TCC              78

ACT CCT AAG CCC TCT CAA CTT TTC CTT CAT GGA AAA CGT             117

AAC AAA ACA TTC AAA GTT TCA TGC AAG GTT ATC AAT AAT             156

AAC GGT AAC CAA GAT GAA ACG AAT TCT GTT GAT CGA AGG             195

AAT GTT CTT CTT GGT TTA GGA GGT CTT TAT GGT GTT GCT             234

AAT GCT ATA CCA TTA GCG GCA TCG GCT ACT CCT ATT CCA             273

TCC CCT GAT CTC AAA ACT TGT GGT AGA GCC ACC ATA TCG             312

GAT GGT CCA CTT GTA CCC TAT TCT TGT TGT CCC CCT CCT             351

ATG CCG ACT AAC TTT GAC ACC ATT CCA TAT TAC AAG TTC             390

CCT TCT ATG ACT AAA CTC CGT ATC CGT ACC CCT GCT CAT             429

GCT GTA GAT GAG GAG TAT ATC GCG AAG TAT AAT TTG GCC             468

ATA AGT CGA ATG AGG GAT CTT GAC AAG ACA GAA CCG TTA             507

AAC CCT CTA GGG TTT AAG CAA CAA GCT AAT ATA CAC TGT             546

GCT TAT TGT AAC GGT GCT TAT ATA ATT GGT GGC AAA GAG             585

TTA CAA GTT CAT AAC TCG TGG CTT TTC TTC CCG TTC CAT             624

CGA TGG TAC TTC TAC TTT TAC GAA AGA ATA TTG GGG AAA             663

CTC ATT GAT GAT CCA ACT TTC GCT TTA CCA TAC TGG AAT             702

TGG GAT CAT CCA AAG GGC ATG CGT TTA CCT CCC ATG TTC             741

GAT CGT GAA GGT TCT TCC CTC TAC GAT GAA AGG CGT AAT             780

CAA CAA GTC CGT AAT GGA ACG GTT TTG GAT CTT GGT TCA             819

TTT GGG GAT AAA GTT GAA ACA ACT CAA CTC CAG TTG ATG             858

AGC AAT AAT TTA ACC CTA ATG TAC CGT CAA ATG GTA ACT             897

AAT GCT CCA TGT CCT CTC TTG TTC TTC GGT GCG CCT TAC             936

GTT CTT GGG AAT AAC GTT GAA GCA CCG GGA ACC ATT GAA             975

ACC ATC CCT CAT ATT CCT GTA CAT ATT TGG GCT GGT ACT            1014

GTC CGT GGT TCA AAA TTT CCT AAC GGT GAT GTG TCC TAC            1053
```

-continued

```
GGT GAG GAT ATG GGT AAT TTC TAC TCA GCT GGT TTG GAC          1092

CCG GTT TTC TAT TGC CAT CAC GGC AAT GTG GAC CGG ATG          1131

TGG AAC GAA TGG AAG GCA ATA GGA GGT AAA AGA AGA GAT          1170

ATA TCT GAA AAG GAT TGG TTG AAC TCC GAG TTC TTT TTC          1209

TAC GAC GAA CAC AAA AAT CCT TAC CGT GTG AAA GTC AGG          1248

GAC TGT TTG GAC ACG AAG AAA ATG GGG TAT GAT TAC GCA          1287

CCA ATG CCA ACT CCA TGG CGT AAT TTC AAA CCA AAA TCA          1326

AAG GCG TCC GTA GGG AAA GTG AAT ACA AGT ACA CTC CCC          1365

CCA GCA AAC GAG GTA TTC CCA CTC GCG AAG ATG GAT AAG          1404

ACT ATT TCA TTT GCT ATC AAC AGG CCA GCT TCA TCG CGG          1443

ACT CAA CAA GAG AAA AAT GAA CAA GAG GAG ATG TTA ACG          1482

TTC AAT AAC ATA AGA TAT GAT AAC AGA GGG TAC ATA AGG          1521

TTC GAT GTG TTC CTG AAC GTG GAC AAC AAT GTG AAC GCG          1560

AAT GAG CTT GAT AAG GCA GAG TTC GCG GGG AGT TAT ACT          1599

AGT TTG CCA CAT GTT CAC AGA GCT GGC GAG AAT GAT CAT          1638

ATC GCG AAG GTT AAT TTC CAG CTG GCG ATA ACA GAA CTG          1677

TTG GAG GAC ATT GGT TTG GAA GAT GAA GAT ACT ATC GCG          1716

GTG ACT CTG GTA CCA AAG AAA GGC GGT GAA GGT ATC TCC          1755

ATT GAG AAT GTG GAG ATC AAG CTT GTG GAT TGT              1788
```

(2) INFORMATION FOR SEQ ID NO:6:

(i) SEQUENCE CHARACTERISTICS:
        (A) LENGTH:    18 base pairs
        (B) TYPE:          nucleic acid
        (C) STRANDEDNESS:   single
        (D) TOPOLOGY:   linear (ii) MOLECULE TYPE:   cDNA (xi) SEQUENCE DESCRIPTION: SEQ ID NO:6:

```
TAATTCGGCA CGAGAGCA                             18
```

(2) INFORMATION FOR SEQ ID NO:7:

(i) SEQUENCE CHARACTERISTICS:
        (A) LENGTH:    189 base pairs
        (B) TYPE:          nucleic acid
        (C) STRANDEDNESS:   single
        (D) TOPOLOGY:   linear (ii) MOLECULE TYPE:   cDNA (xi) SEQUENCE DESCRIPTION: SEQ ID NO:7:

```
TAAGTCTCAA TTGAATTTGC TGAGATTACA ATTATGATGG ATGATGATAT          50

GTTTTTATGT TACTTTTGTT CTGTTATCTA CTTTTGCTTT TCTCGTGTAA         100

CTTTTCCTGT TGAAATCACC CTACATGCTT GATTTCCTTG GAGTTGTTAT         150

TCACTAATAA ATCAGTTAGG TTAAAAAAAA AAAAAAAA                     189
```

(2) INFORMATION FOR SEQ ID NO:8:

(i) SEQUENCE CHARACTERISTICS:
        (A) LENGTH:    596 amino acids

```
            (B) TYPE:              amino acid
            (C) STRANDEDNESS:      single
            (D) TOPOLOGY:          linear (ii) MOLECULE TYPE:    peptide (xi) SEQUENCE DESCRIPTION: SEQ ID NO:8:

Met Ala Ser Val Val Cys Asn Ser Ser Ser Thr Thr Thr Thr
              5                  10                  15

Thr Leu Lys Thr Pro Phe Thr Ser Leu Gly Ser Thr Pro Lys Pro
             20                  25                  30

Ser Gln Leu Phe Leu His Gly Lys Arg Asn Lys Thr Phe Lys Val
             35                  40                  45

Ser Cys Lys Val Ile Asn Asn Asn Gly Asn Gln Asp Glu Thr Asn
             50                  55                  60

Ser Val Asp Arg Arg Asn Val Leu Leu Gly Leu Gly Gly Leu Tyr
             65                  70                  75

Gly Val Ala Asn Ala Ile Pro Leu Ala Ala Ser Ala Thr Pro Ile
             80                  85                  90

Pro Ser Pro Asp Leu Lys Thr Cys Gly Arg Ala Thr Ile Ser Asp
             95                 100                 105

Gly Pro Leu Val Pro Tyr Ser Cys Cys Pro Pro Met Pro Thr
            110                 115                 120

Asn Phe Asp Thr Ile Pro Tyr Tyr Lys Phe Pro Ser Met Thr Lys
            125                 130                 135

Leu Arg Ile Arg Thr Pro Ala His Ala Val Asp Glu Glu Tyr Ile
            140                 145                 150

Ala Lys Tyr Asn Leu Ala Ile Ser Arg Met Arg Asp Leu Asp Lys
            155                 160                 165

Thr Glu Pro Leu Asn Pro Leu Gly Phe Lys Gln Gln Ala Asn Ile
            170                 175                 180

His Cys Ala Tyr Cys Asn Gly Ala Tyr Ile Ile Gly Gly Lys Glu
            185                 190                 195

Leu Gln Val His Asn Ser Trp Leu Phe Phe Pro Phe His Arg Trp
            200                 205                 210

Tyr Phe Tyr Phe Tyr Glu Arg Ile Leu Gly Lys Leu Ile Asp Asp
            215                 220                 225

Pro Thr Phe Ala Leu Pro Tyr Trp Asn Trp Asp His Pro Lys Gly
            230                 235                 240

Met Arg Leu Pro Pro Met Phe Asp Arg Glu Gly Ser Ser Leu Tyr
            245                 250                 255

Asp Glu Arg Arg Asn Gln Gln Val Arg Asn Gly Thr Val Leu Asp
            260                 265                 270

Leu Gly Ser Phe Gly Asp Lys Val Glu Thr Thr Gln Leu Gln Leu
            275                 280                 285

Met Ser Asn Asn Leu Thr Leu Met Tyr Arg Gln Met Val Thr Asn
            290                 295                 300

Ala Pro Cys Pro Leu Leu Phe Gly Ala Pro Tyr Val Leu Gly
            305                 310                 315

Asn Asn Val Glu Ala Pro Gly Thr Ile Glu Thr Ile Pro His Ile
            320                 325                 330

Pro Val His Ile Trp Ala Gly Thr Val Arg Gly Ser Lys Phe Pro
            335                 340                 345

Asn Gly Asp Val Ser Tyr Gly Glu Asp Met Gly Asn Phe Tyr Ser
            350                 355                 360
```

```
Ala Gly Leu Asp Pro Val Phe Tyr Cys His His Gly Asn Val Asp
            365                 370                 375

Arg Met Trp Asn Glu Trp Lys Ala Ile Gly Gly Lys Arg Arg Asp
            380                 385                 390

Ile Ser Glu Lys Asp Trp Leu Asn Ser Glu Phe Phe Phe Tyr Asp
            395                 400                 405

Glu His Lys Asn Pro Tyr Arg Val Lys Val Arg Asp Cys Leu Asp
            410                 415                 420

Thr Lys Lys Met Gly Tyr Asp Tyr Ala Pro Met Pro Thr Pro Trp
            425                 430                 435

Arg Asn Phe Lys Pro Lys Ser Lys Ala Ser Val Gly Lys Val Asn
            440                 445                 450

Thr Ser Thr Leu Pro Pro Ala Asn Glu Val Phe Pro Leu Ala Lys
            455                 460                 465

Met Asp Lys Thr Ile Ser Phe Ala Ile Asn Arg Pro Ala Ser Ser
            470                 475                 480

Arg Thr Gln Gln Glu Lys Asn Glu Gln Glu Glu Met Leu Thr Phe
            485                 490                 495

Asn Asn Ile Arg Tyr Asp Asn Arg Gly Tyr Ile Arg Phe Asp Val
            500                 505                 510

Phe Leu Asn Val Asp Asn Asn Val Asn Ala Asn Glu Leu Asp Lys
            515                 520                 525

Ala Glu Phe Ala Gly Ser Tyr Thr Ser Leu Pro His Val His Arg
            530                 535                 540

Ala Gly Glu Asn Asp His Ile Ala Lys Val Asn Phe Gln Leu Ala
            545                 550                 555

Ile Thr Glu Leu Leu Glu Asp Ile Gly Leu Glu Asp Glu Asp Thr
            560                 565                 570

Ile Ala Val Thr Leu Val Pro Lys Lys Gly Gly Glu Gly Ile Ser
            575                 580                 585

Ile Glu Asn Val Glu Ile Lys Leu Val Asp Cys
            590                 595

(2) INFORMATION FOR SEQ ID NO:9:

(i) SEQUENCE CHARACTERISTICS:
        (A) LENGTH:       14 amino acids
        (B) TYPE:             amino acid
        (C) STRANDEDNESS:     single
        (D) TOPOLOGY:     linear (ii) MOLECULE TYPE:    peptide (xi) SEQUENCE DESCRIPTION: SEQ ID NO:9:

Ala Pro Ile Pro Pro Asp Leu Lys Ser Gly Gly Thr Ala
1               5                   10

(2) INFORMATION FOR SEQ ID NO:10:

(i) SEQUENCE CHARACTERISTICS:
        (A) LENGTH:       14 amino acids
        (B) TYPE:             amino acid
        (C) STRANDEDNESS:     single
        (D) TOPOLOGY:     linear (ii) MOLECULE TYPE:    peptide (xi) SEQUENCE DESCRIPTION: SEQ ID NO:10:

Ala Pro Ile Pro Pro Asp Leu Lys Ser Asp Xaa Thr Ala
```

```
   1               5                   10
```

(2) INFORMATION FOR SEQ ID NO:11:

(i) SEQUENCE CHARACTERISTICS:
        (A) LENGTH:      15 amino acids
        (B) TYPE:                amino acid
        (C) STRANDEDNESS:        single
        (D) TOPOLOGY:    linear (ii) MOLECULE TYPE:    peptide (xi) SEQUENCE DESCRIPTION: SEQ ID NO:11:

```
Ala Pro Ile Pro Pro Pro Asp Leu Lys Ser Gln Gly Thr Ala His
              5                   10                  15
```

(2) INFORMATION FOR SEQ ID NO:12:

(i) SEQUENCE CHARACTERISTICS:
        (A) LENGTH:      15 amino acids
        (B) TYPE:                amino acid
        (C) STRANDEDNESS:        single
        (D) TOPOLOGY:    linear (ii) MOLECULE TYPE:    peptide (xi) SEQUENCE DESCRIPTION: SEQ ID NO:12:

```
Ala Pro Ile Pro Pro Pro Asp Leu Lys Ser Gln Gly Thr Ala His
 1            5                   10                  15
```

(2) INFORMATION FOR SEQ ID NO:13:

(i) SEQUENCE CHARACTERISTICS:
        (A) LENGTH:      19 amino acids
        (B) TYPE:                amino acid
        (C) STRANDEDNESS:        single
        (D) TOPOLOGY:    linear (ii) MOLECULE TYPE:    peptide (xi) SEQUENCE DESCRIPTION: SEQ ID NO:13:

```
Ser Pro Ile Pro Pro Pro Asp Leu Lys Ser Xaa Gly Val Ala His
              5                   10                  15
Tyr Lys Glu Pro
         19
```

(2) INFORMATION FOR SEQ ID NO:14:

(i) SEQUENCE CHARACTERISTICS:
        (A) LENGTH:      1764 base pairs
        (B) TYPE:                nucleic acid
        (C) STRANDEDNESS:        single
        (D) TOPOLOGY:    linear (ii) MOLECULE TYPE:    cDNA (xi) SEQUENCE DESCRIPTION: SEQ ID NO:14:

```
TCT TCT TCT AGT ACT ACT ACT ATT CCA TTA TGC ACC AAC             39

AAA TCC CTC TCT TCT TCC TTC ACC ACC AAC AAC TCA TCT             78

TTC TTA TCA AAA CCC TCT CAA CTT TTC CTC CAC GGA AGG            117

CGT AAT CAA AGT TTC AAG GTT TCA TGC AAC GCC AAC AAT            156

AAT GTT GGC GAG CAT GAC AAA AAC CTT GAC ACT GTT GAT            195

AGG CGA AAT GTT CTT TTA GGG TTA GGA GGT CTT TAT GGT            234

GCT GCT AAT CTT GCA CCA TTA GCC TCT GCT TCT CCT ATA            273
```

-continued

```
CCA CCT CCT GAT CTA AAA TCT TGT GGT GTT GCC CAT GTA        312
ACA GAA GGT GTT GAT GTG ACA TAT AGT TGT TGC CCA CCT        351
GTA CCC GAT GAT ATC GAT AGC GTT CCG TAC TAC AAG TTC        390
CCT CCT ATG ACT AAA CTC CGC ATC CGC CCC CCT GCT CAT        429
GCG GCG GAT GAG GAG TAT GTA GCC AAG TAT CAA TTG GCT        468
ACG AGT CGA ATG AGG GAA CTT GAT AAA GAC TCT TTT GAC        507
CCT CTT GGG TTT AAA CAA CAA GCT AAT ATT CAT TGT GCT        546
TAT TGT AAC GGT GCT TAT AAA GTT GGT GGT AAA GAG TTG        585
CAA GTT CAT TTC TCG TGG CTT TTC TTT CCG TTT CAT AGA        624
TGG TAC TTG TAT TTC TAT GAA AGA ATA TTG GGA TCA CTT        663
ATT AAT GAT CCA ACT TTT GCT TTA CCA TAT GGA AAT TGG        702
GAT CAT CCA AAA GGT ATG CGT ATA CCT CCC ATG TTT GAT        741
CGT GAG GGG TCA TCT CTT TAC GAT GAT AAA CGT AAC CAA        780
AAC CAT CGC AAT GGA ACT ATT ATT GAT CTT GGT CAT TTT        819
GGT CAG GAA GTT GAC ACA CCT CAG CTT CAG ATA ATG ACT        858
AAT AAT TTA ACA CTA ATG TAC CGT CAA ATG GTC ACT AAT        897
GCT CCT TGT CCG TCC CAA TTC TTC GGT GCT GCT TAC CTC        936
TGG GGA CTG AAC CAA GTC CAG GAA TGG GTA CTA TTG AGA        975
ACA TCC CTC ATA CCC CGT GCC ATA TCT GGA CTG GTG ATA       1014
GTC CTA GAC AAA AAA ACG GTG AAA ACA TGG GTA ATT TCT       1053
ATT CAG CAC GGT TTA GAC CCG ATT TTT TAC TGT CAC CAC       1092
GCA AAT GTG GAC CGG ATG TGG GAT GAA TGG AAA TTA ATT       1131
GGC GGG AAA AGA AGG GAT CTA TCA AAT AAA GAT TGG TTG       1170
AAC TCA GAA TTC TTT TTC TAC GAT GAA AAT CGC AAC CCT       1209
TAC CGT GTG AAA GTC CGT GAC TGT TTG GAC AGT AAA AAA       1248
ATG GGA TTC AGT TAC GCT CCA ATG CCA ACT CCA TGG CGT       1287
AAT TTT AAA CCA ATC AGA AAA ACT ACA GCA GGA AAA GTG       1326
AAT ACA GCG TCA ATT GCA CCA GTC ACC AAG GTG TTC CCA       1365
CTA GCG AAG CTG GAC CGT GCA ATT TCG TTC TCT ATC ACC       1404
AGA CCA GCT TCG TCA AGG ACT ACA CAG GAG AAA AAT GAG       1443
CAA GAG GAG ATA CTG ACA TTC AAC AAA GTA GCC TAT GAT       1482
GAT ACT AAG TAT GTA AGG TTC GAT GTG TTC CTG AAC GTT       1521
GAC AAG ACT GTG AAT GCG GAT GAG CTT GAT AAG GCG GAG       1560
TTT GCG GGG AGT TAT ACT AGC TTG CCG CAT GTT CAT GGA       1599
AAT AAT ACT AAT CAT GTT ACG AGT GTT ACT TTC AAG CTG       1638
GCG ATA ACA GAA CTG TTG GAG GAT AAT GGA TTG GAA GAT       1677
GAA GAT ACT ATT GCG GTA ACT TTG GTT CCA AAA GTT GGT       1716
GGT GAA GGT GTA TCC ATT GAA AGT GTG GAG ATC AAG CTT       1755
GAG GAT TGT                                                1764
```

(2) INFORMATION FOR SEQ ID NO:15:

(i) SEQUENCE CHARACTERISTICS:
        (A) LENGTH: 222 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
TAAGTCCTCA TGAGTTGGTG GCTATGGTAC CAAATTTTAT GTTTAATTAT           50

ATTAATGTGT GTGTTTGATT ATGTTTCGGT TAAAATGTAT CAGCTGGATA          100

GCTGATTACT AGCCTTCCCA GTTGTTAATG CTATGTATGA AATAAATAAA          150

TAAATGGTTG TCTTCCATTT AATTTTAAAA AAAAAAAAAA AAAAAAAAA           200

AAAAAAAAAA AAAAAAAAA AA                                         222
```

(2) INFORMATION FOR SEQ ID NO:16:

(i) SEQUENCE CHARACTERISTICS:
        (A) LENGTH: 588 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Ser Ser Ser Ser Thr Thr Thr Ile Pro Leu Tyr Thr Asn Lys Ser
                 5                  10                  15

Leu Ser Ser Ser Phe Thr Thr Asn Asn Ser Ser Phe Leu Ser Lys
                20                  25                  30

Pro Ser Gln Leu Phe Leu His Gly Arg Arg Asn Gln Ser Phe Lys
                35                  40                  45

Val Ser Tyr Asn Ala Asn Asn Asn Val Gly Glu His Asp Lys Asn
                50                  55                  60

Leu Asp Thr Val Asp Arg Arg Asn Val Leu Leu Gly Leu Gly Gly
                65                  70                  75

Leu Tyr Gly Ala Ala Asn Leu Ala Pro Leu Ala Ser Ala Ser Pro
                80                  85                  90

Ile Pro Pro Pro Asp Leu Lys Ser Cys Gly Val Ala His Val Thr
                95                 100                 105

Glu Gly Val Asp Val Thr Tyr Ser Cys Tyr Pro Pro Val Pro Asp
               110                 115                 120

Asp Ile Asp Ser Val Pro Tyr Tyr Lys Phe Pro Pro Met Thr Lys
               125                 130                 135

Leu Arg Ile Arg Pro Pro Ala His Ala Ala Asp Glu Glu Tyr Val
               140                 145                 150

Ala Lys Tyr Gln Leu Ala Thr Ser Arg Met Arg Glu Leu Asp Lys
               155                 160                 165

Asp Ser Phe Asp Pro Leu Gly Phe Lys Gln Gln Ala Asn Ile His
               170                 175                 180

Cys Ala Tyr Cys Asn Gly Ala Tyr Lys Val Gly Lys Glu Leu
               185                 190                 195

Gln Val His Phe Ser Trp Leu Phe Phe Pro Phe His Arg Trp Tyr
               200                 205                 210

Leu Tyr Phe Tyr Glu Arg Ile Leu Gly Ser Leu Ile Asn Asp Pro
```

```
                215                 220                 225
Thr Phe Ala Leu Pro Tyr Trp Asn Trp Asp His Pro Lys Gly Met
                230                 235                 240
Arg Ile Pro Pro Met Phe Asp Arg Glu Gly Ser Ser Leu Tyr Asp
                245                 250                 255
Asp Lys Arg Asn Gln Asn His Arg Asn Gly Thr Ile Ile Asp Leu
                260                 265                 270
Gly His Phe Gly Gln Glu Val Asp Thr Pro Gln Leu Gln Ile Met
                275                 280                 285
Thr Asn Asn Leu Thr Leu Met Tyr Arg Gln Met Val Thr Asn Ala
                290                 295                 300
Pro Cys Pro Ser Gln Phe Phe Gly Ala Ala Tyr Leu Trp Gly Leu
                305                 310                 315
Asn Gln Val Gln Glu Trp Val Leu Leu Arg Thr Ser Leu Ile Pro
                320                 325                 330
Arg Ala Ile Ser Gly Leu Val Ile Val Leu Asp Lys Lys Thr Val
                335                 340                 345
Lys Thr Trp Val Ile Ser Ile Gln His Gly Leu Asp Pro Ile Phe
                350                 355                 360
Tyr Cys His His Ala Asn Val Asp Arg Met Trp Asp Glu Trp Lys
                365                 370                 375
Leu Ile Gly Gly Lys Arg Arg Asp Leu Ser Asn Lys Asp Trp Leu
                380                 385                 390
Asn Ser Glu Phe Phe Phe Tyr Asp Glu Asn Arg Asn Pro Tyr Arg
                395                 400                 405
Val Lys Val Arg Asp Cys Leu Asp Ser Lys Lys Met Gly Phe Ser
                410                 415                 420
Tyr Ala Pro Met Pro Thr Pro Trp Arg Asn Phe Lys Pro Ile Arg
                425                 430                 435
Lys Thr Thr Ala Gly Lys Val Asn Thr Ala Ser Ile Ala Pro Val
                440                 445                 450
Thr Lys Val Phe Pro Leu Ala Lys Leu Asp Arg Ala Ile Ser Phe
                455                 460                 465
Ser Ile Thr Arg Pro Ala Ser Ser Arg Thr Thr Gln Glu Lys Asn
                470                 475                 480
Glu Gln Glu Glu Ile Leu Thr Phe Asn Lys Val Ala Tyr Asp Asp
                485                 490                 495
Thr Lys Tyr Val Arg Phe Asp Val Phe Leu Asn Val Asp Lys Thr
                500                 505                 510
Val Asn Ala Asp Glu Leu Asp Lys Ala Glu Phe Ala Gly Ser Tyr
                515                 520                 525
Thr Ser Leu Pro His Val His Gly Asn Asn Thr Asn His Val Thr
                530                 535                 540
Ser Val Thr Phe Lys Leu Ala Ile Thr Glu Leu Leu Glu Asp Asn
                545                 550                 555
Gly Leu Glu Asp Glu Asp Thr Ile Ala Val Thr Leu Val Pro Lys
                560                 565                 570
Val Gly Gly Glu Gly Val Ser Ile Glu Ser Val Glu Ile Lys Leu
                575                 580                 585
Glu Asp Cys
        588

(2) INFORMATION FOR SEQ ID NO:17:
```

(i) SEQUENCE CHARACTERISTICS:
  (A) LENGTH: 1749 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:17:

| | |
|---|---:|
| ACT ACT CTT CCA TTA TGC AAC AAC AAA TCC CTC TCT TCT | 39 |
| TCC TTC ACC ACC AAC AAC TCA TCT TTC TTA TCA AAA CCC | 78 |
| TCT CAA CTT TTC CTC CAC GGA AGG CGT AAT CAA AGT TTC | 117 |
| AAG GTT TCA TGC AAC GCC AAC AAT AAT GTT GGC GAG CAT | 156 |
| GAC AAA AAC CTT GAC GCT GTT GAT AGG CGA AAT GTT CTT | 195 |
| TTA GGG TTA GGA GGT CTT TAT GGT GCT GCT AAT CTT GCA | 234 |
| CCA TTA GCC TCT GCT TCT CCT ATA CCA CCT CCT GAT CTA | 273 |
| AAA TCT TGT GGT GTT GCC CAT GTA AAA GAA GGT GTT GAT | 312 |
| GTG TCA TAC AGT TGT TGC CCT CCT GTA CCC GAT GAT ATC | 351 |
| GAT AGC GTT CCG TAC TAC AAG TTC CCT TCT ATG ACT AAA | 390 |
| CTC CGC ATC CGC CCC CCT GCT CAT GCG GCG GAT GAG GAG | 429 |
| TAT GTA GCC AAG TAT CAA TTG GCT ACG AGT CGA ATG AGG | 468 |
| GAA CTT GAT AAA GAC TCT TTT GAC CCT CTT GGG TTT AAA | 507 |
| CAA CAA GCT AAT ATT CAT TGT GCT TAT TGT AAC GGT GCT | 546 |
| TAT AAA GTT GGT GGT AAA GAG TTG CAA GTT CAT TTC TCG | 585 |
| TGG CTT TTC TTT CCG TTT CAT AGA TGG TAC TTG TAC TTC | 624 |
| TAC GAA AGA ATT TTG GGA TCA CTT ATT AAT GAT CCA ACT | 663 |
| TTT GCT TTA CCA TAT GGG AAT TGG GAT CAT CCA AAA GGT | 702 |
| ATG CGT ATA CCT CCC ATG TTT GAT CGT GAG GGG TCA TCT | 741 |
| CTT TAC GAT GAT AAA CGT AAC CAA AAC CAT CGC AAT GGA | 780 |
| ACT ATT ATT GAT CTT GGT CAT TTT GGT AAG GAA GTT GAC | 819 |
| ACA CCT CAG CTC CAG ATA ATG ACT AAT AAT TTA ACA CTA | 858 |
| ATG TAC CGT CAA ATG GTC ACT AAT GCT CCT TGT CCG TCC | 897 |
| CAA TTC TTC GGT GCT GCT TAC CTC TGG GGA CTG AAC CAA | 936 |
| GTC CGG GAC AGG GTA CTA TTG AGA ACA TCC CTC ATA CTC | 975 |
| CGG TTC ACA TCT GGA CCG GTG ACA AAC CTC GAC AAA AAA | 1014 |
| ACG GTG AAA ACA TGG GTA ATT TCT ATT CAG CAC GGT TTA | 1053 |
| GAC CCG CTT TTT TAC TGT CAC CAT GCA AAT GTG GAC CGG | 1092 |
| ATG TGG GAT GAA TGG AAA TTA ATT GGT GGG AAA AGA AGG | 1131 |
| GAT CTA TCA AAT AAA GAT TGG TTG AAC TCA GAA TTC TTT | 1170 |
| TTC TAC GAT GAA AAT CGC AAC CCT TAC CGT GTG AAA GTC | 1209 |
| CGT GAC AGT TTG GAC AGT AAA AAA ATG GGA TTC AGT TAC | 1248 |
| GCT CCA ATG CCA ACT CCA TGG CGT AAT TTT AAA CCA ATC | 1287 |
| AGA AAA ACT ACA GCA GGA ATA GTG AAT ACA GCG TCA ATT | 1326 |

-continued

```
GCA CCA GTC ACC AAG GTG TTC CCA CTG GCG AAG CTG GAC        1365

CGT GCG ATT TCA TTC TCT ATC ACC AGA CCA GCT TCG TCA        1404

AGG ACT ACG CAG GAG AAA AAT GAG CAA GAG GAG ATA CTG        1443

ACA TTC AAA AAG ATA GCC TAT GAT GAT ACT CAG TAT GTA        1482

AGG TTC GAT GTG TTC CTG AAC GTT GAC AAG ACT GTG AAT        1521

GCG GAT GAG CTT GAT AAG GCA GAG TTT GCG GGG AGT TAT        1560

ACT AGC TTG CCG CAT GTT CAT GGA AAT AAT ACT AAT CAT        1599

GCT ACG AGT GTT ACT TTC ACA GCT GGC ATA ACA GAA CTG        1638

TTG GAG GAT ATT GGA TTG GAA GAT GAA GAT ACT ATT GCG        1677

GTA ACT TTG GTT CCA AAA GTA GGT GGT GAA GGT GTA TCC        1716

ATT GAA AGT GTG GAG ATC AAG CTT GAG GAT TGT                1749
```

(2) INFORMATION FOR SEQ ID NO:18:

(i) SEQUENCE CHARACTERISTICS:
        (A) LENGTH:      173 base pairs
        (B) TYPE:             nucleic acid
        (C) STRANDEDNESS:     single
        (D) TOPOLOGY:     linear (ii) MOLECULE TYPE:     cDNA (xi) SEQUENCE DESCRIPTION: SEQ ID NO:18:

```
TAAGTCCTCA TGAGTTGGTG GCTATGGTAC CAAATTTTAT GTTTAATTAG        50

TATTAATGTG TGTATGTGTT GATTATGTTT CGGGTAAAAT GTATCAGCTG       100

GATAGCTGAT TACTAGCCTT GCCAGTTGTT AATGCTATGT ATGAAATAAA       150

TAAATAAAAA AAAAAAAAAA AAA                                    173
```

(2) INFORMATION FOR SEQ ID NO:19:

(i) SEQUENCE CHARACTERISTICS:
        (A) LENGTH:      583 amino acids
        (B) TYPE:             amino acid
        (C) STRANDEDNESS:     single
        (D) TOPOLOGY:     linear (ii) MOLECULE TYPE:     peptide (xi) SEQUENCE DESCRIPTION: SEQ ID NO:19:

```
Thr Thr Leu Pro Leu Cys Asn Asn Lys Ser Leu Ser Ser Phe
 1               5                  10                  15

Thr Thr Asn Asn Ser Ser Phe Leu Ser Lys Pro Ser Gln Leu Phe
                20                  25                  30

Leu His Gly Arg Arg Asn Gln Ser Phe Lys Val Ser Cys Asn Ala
            35                  40                  45

Asn Asn Asn Val Gly Glu His Asp Lys Asn Leu Asp Ala Val Asp
        50                  55                  60

Arg Arg Asn Val Leu Leu Gly Leu Gly Gly Leu Tyr Gly Ala Ala
        65                  70                  75

Asn Leu Ala Pro Leu Ala Ser Ala Ser Pro Ile Pro Pro Asp
            80                  85                  90

Leu Lys Ser Cys Gly Val Ala His Val Lys Glu Gly Val Asp Val
                95                 100                 105

Ser Tyr Ser Cys Cys Pro Pro Val Pro Asp Asp Ile Asp Ser Val
                110                115                 120
```

-continued

```
Pro Tyr Tyr Lys Phe Pro Ser Met Thr Lys Leu Arg Ile Arg Pro
            125                 130                 135

Pro Ala His Ala Ala Asp Glu Glu Tyr Val Ala Lys Tyr Gln Leu
            140                 145                 150

Ala Thr Ser Arg Met Arg Glu Leu Asp Lys Asp Ser Phe Asp Pro
            155                 160                 165

Leu Gly Phe Lys Gln Gln Ala Asn Ile His Cys Ala Tyr Cys Asn
            170                 175                 180

Gly Ala Tyr Lys Val Gly Gly Lys Glu Leu Gln Val His Phe Ser
            185                 190                 195

Trp Leu Phe Phe Pro Phe His Arg Trp Tyr Leu Tyr Phe Tyr Glu
            200                 205                 210

Arg Ile Leu Gly Ser Leu Ile Asn Asp Pro Thr Phe Ala Leu Pro
            215                 220                 225

Tyr Trp Asn Trp Asp His Pro Lys Gly Met Arg Ile Pro Pro Met
            230                 235                 240

Phe Asp Arg Glu Gly Ser Ser Leu Tyr Asp Asp Lys Arg Asn Gln
            245                 250                 255

Asn His Arg Asn Gly Thr Ile Ile Asp Leu Gly His Phe Gly Lys
            260                 265                 270

Glu Val Asp Thr Pro Gln Leu Gln Ile Met Thr Asn Asn Leu Thr
            275                 280                 285

Leu Met Tyr Arg Gln Met Val Thr Asn Ala Pro Cys Pro Ser Gln
            290                 295                 300

Phe Phe Gly Ala Ala Tyr Leu Trp Gly Leu Asn Gln Val Arg Asp
            305                 310                 315

Arg Val Leu Leu Arg Thr Ser Leu Ile Leu Arg Phe Thr Ser Gly
            320                 325                 330

Pro Val Thr Asn Leu Asp Lys Lys Thr Val Lys Thr Trp Val Ile
            335                 340                 345

Ser Ile Gln His Gly Leu Asp Pro Leu Phe Tyr Cys His His Ala
            350                 355                 360

Asn Val Asp Arg Met Trp Asp Glu Trp Lys Leu Ile Gly Gly Lys
            365                 370                 375

Arg Arg Asp Leu Ser Asn Lys Asp Trp Leu Asn Ser Glu Phe Phe
            380                 385                 390

Phe Tyr Asp Glu Asn Arg Asn Pro Tyr Arg Val Lys Val Arg Asp
            395                 400                 405

Ser Leu Asp Ser Lys Lys Met Gly Phe Ser Tyr Ala Pro Met Pro
            410                 415                 420

Thr Pro Trp Arg Asn Phe Lys Pro Ile Arg Lys Thr Thr Ala Gly
            425                 430                 435

Ile Val Asn Thr Ala Ser Ile Ala Pro Val Thr Lys Val Phe Pro
            440                 445                 450

Leu Ala Lys Leu Asp Arg Ala Ile Ser Phe Ser Ile Thr Arg Pro
            455                 460                 465

Ala Ser Ser Arg Thr Thr Gln Glu Lys Asn Glu Gln Glu Glu Ile
            470                 475                 480

Leu Thr Phe Lys Lys Ile Ala Tyr Asp Asp Thr Gln Tyr Val Arg
            485                 490                 495

Phe Asp Val Phe Leu Asn Val Asp Lys Thr Val Asn Ala Asp Glu
            500                 505                 510
```

```
Leu Asp Lys Ala Glu Phe Ala Gly Ser Tyr Thr Ser Leu Pro His
            515                 520                 525

Val His Gly Asn Asn Thr Asn His Ala Thr Ser Val Thr Phe Thr
            530                 535                 540

Ala Gly Ile Thr Glu Leu Leu Glu Asp Ile Gly Leu Glu Asp Glu
            545                 550                 555

Asp Thr Ile Ala Val Thr Leu Val Pro Lys Val Gly Gly Glu Gly
            560                 565                 570

Val Ser Ile Glu Ser Val Glu Ile Lys Leu Glu Asp Cys
            575                 580
```

POLYPHENOL OXIDASE CDNA

The subject application is a continuation of application Ser. No. 08/203,533, filed Feb. 28, 1994, now abandoned, which was a continuation-in-part of application Ser. No. 07/833,839, filed Jan. 31, 1992, now abandoned.

BACKGROUND OF THE INVENTION

Polyphenol oxidases (PPO) are ubiquitous copper metalloenzymes of angiosperms which catalyze the oxidation of phenols to quinones at the expense of $O_2$. More specifically these enzymes catalyze the o-hydroxylation of a monophenol followed by its oxidation to the o-diquinone (cresolase activity [E.C. 1.14.18.1]), or the oxidation of an o-dihydroxyphenol to the o-diquinone (catecholase activity [E.C. 1.10.3.2]). Although PPOs may possess both catecholase and cresolase activities, typically the cresolase activity is absent, labile, or requires priming with reducing agent or small amounts of an o-dihydroxyphenol. The quinonoid reaction products formed by PPO are highly reactive, electrophilic molecules which undergo secondary reactions with themselves or act to covalently modify and crosslink a variety of cellular nucleophiles, including nucleophiles of proteins such as sulfhydryl, amine, amide, indole and imidazole substituents. The formation of quinone adducts (usually brown or black colored) represents the primary detrimental effect of PPO in post harvest physiology and food processing and is the primary reason for the interest in PPOs in food technology. [See Adv. Food Res 19:75 (1971)]. In the cultivated potato alone, melanization driven by PPO is responsible for significant losses each year in potato processing (prepeel blackening, blackspot, pressure bruising and blackheart). Sulfite or ascorbate additives used in the food, wine and beverage industry are frequently employed to inhibit activity of PPO. Conversely, the ability of quinones to covalently modify and reduce the nutritive value of plant proteins has generated interest in PPO for increasing the herbivore resistance of plants [see Naturally Occurring Pest Bioregulators, pp 166–197, ACE Books, Washington (1991)].

Despite the intense study of PPO since its first description in 1895, a large number of biochemical and physiological studies have provided few answers to the question of PPO function and expression. The primary obstacle to understanding PPO function is the formation of artifactual protein species and enzyme inactivation due to quinone adduct formation and PPO crosslinking during isolation and purification. Thus, rapid quinone formation makes it exceptionally difficult to isolate an unmodified PPO, and this problem is a significant factor contributing to the high and varying estimates of the number and properties of higher plant PPOs. In addition, the difficulty of obtaining PPO-null plants has thus far minimized the contribution of genetics to understanding the function and expression of these enzymes.

A variety of hypotheses concerning the function of PPO have been proposed since the first recognition of its activity in 1895. These proposed functions relate to the oxygen reduction activity of PPO as well as its ability to oxidize phenolics to quinones. PPO has been proposed to be involved in buffering of plastid oxygen levels, biosynthesis of phenolics, wound healing, and anti-nutritive modifications of plant proteins to discourage herbivory [see Naturally Occurring Pest Bioregulators, pp 166–197, ACS Books, Washington, D.C. (1991)].

PPO is present in many organs and tissues. It is often abundant in leaves, tubers, storage roots, floral parts and fruits. The abundance of PPO in tubers and fruits at early stages of development along with high levels of phenolic substrates has led to suggestions of a possible role for PPO in making the unripe fruit and storage organs inedible to predators [see Recent Advances in Biochemistry of Fruit and Vegetables, pp 159–180, Academic Press (1981)]. PPO has been detected in root plastids, potato amyloplasts, leucoplasts, etioplasts and chromoplasts, as well as in plastid-like particles isolated from sugar beet leaves [see Israel J. Bot. 12:74 (1964)].

Most studies indicate that PPO is membrane-bound in plastids of non-senescing tissues [see Phytochemistry 26:1 (1987)]. PPO activity is frequently latent, requiring activation by proteolysis, detergent, or $Ca^{++}$ it has been suggested that the enzyme is located exclusively in plastids preventing its interaction with phenolics until the cell is disrupted in some way. Thus, PPO is only released to the cytosol upon wounding, senescence or deterioration of the organelle [see Photobiochem. Photobiophys 3:69 (1981), and Physiol Plant 72:659 (1988)].

Although PPO is encoded by nuclear genes [see J. Heredity 81:475 (1990)], very little is known about the targeting and import of PPO to organelles, its insertion into organellar membranes and the spatial arrangement of the enzyme within the membrane.

In Sorghum (a C4 plant) leaves, PPO has been detected only in mesophyll cells; it was absent from bundle sheath cells. Considering the distribution of thylakoid grana stacks and PSII activity, this observation suggests a possible functional association of PPO with photosynthetic activity. However, PPO is also present in cells of many non-photosynthetic organs, such as roots, tubers, fruit, etc. In non-photosynthetic plastids, or plastids treated with tentoxin, PPO has been detected in vesicles which appeared to be attached to the plastid envelope. These observations, along with latency phenomena and the marked changes often observed in PPO levels during development, suggest that regulation of PPO expression is quite complex and may operate on several levels.

Several function have been proposed to explain the role of PPOs in plants. Based on its location on the thylakoid membrane and high $K_m$ for $O_2$, PPO has been proposed to function in pseudocyclic photophosphorylation (ATP production with PPO as a terminal electron acceptor rather than $NADP^+$), and regulation of plastidic oxygen levels. However, there is no evidence for a suitable substrate for PPO in this compartment which could allow a PPO-based oxygen reduction cycle to operate.

In contrast, the role of PPO in polymerization of trichome exudate and insect entrapment is relatively well established. [see Insects and The Plant Surface, pp 151–172, Edward Arnold, London (1986)]. In solanaceous plants, PPO is the dominant protein and oxidative enzyme of glandular trichomes (ca. 40–80% of total trichome protein) and appears to be responsible for the $O_2$-requiring polymerization of trichome exudate which results in insect entrapment, and therefore, resistance to insect feeding [see PANS 23:272 (1977) and Naturally Occurring Pest Bioregulators, pp 166–197, ACS Books, Washington, D.C. (1991)].

A third possible function for PPO in plant tissues is that sequestration of PPO in the thylakoid prevents its interaction with phenolics until the cell is disrupted by herbivores, pathogens, senescence, or other injury. The quinones thus generated by PPO activity on phenolics cross-link with themselves and protein to reduce the palatability, digestibility, and nutritive value of the plant tissue and its protein to other organisms. This alternative view suggests that the primary targets of quinones formed by PPO are the nucleophilic amino acids: histidine, cysteine, methionine, tryptophan, and lysine. The low abundance of these essential amino acids in plant proteins limits insect growth on plant diets. Covalent modification of these essential amino acids by PPO-generated quinones further decreases their nutritional availability to herbivores and may result in poorer insect performance. In addition, quinone-modified protein is thought to be less attractive or palatable to herbivores thereby discouraging feeding. The ability of PPOs to covalently modify plant proteins upon wounding has led to their designation as being "antinutritive enzymes" which function in plant pest resistance in a manner complementary to the inducible proteinase inhibitors of plants.

SUMMARY OF THE INVENTION

The subject invention provides PPO cDNAs which can be ligated into an array of vectors used for transformation of plants (for example, vectors based on *Agrobacterium tumefaciens* [see Nature 310:115]) to achieve either overexpression or down-regulation of PPO. Overexpression is achieved by ligation of the PPO cDNA in a "sense" orientation using promoters such as the 35S promoter of cauliflower mosaic virus [see Plant Cell 2:7]. Alternatively, down-regulation of PPO can be obtained by ligating the PPO cDNA, or some fragment of this sequence, to a similar promoter in an "antisense" orientation [see Plant Molecular Biology 11:301; Gene 72:45; Plant Molecular Biology 14:457; Cell 55:673; and Nature 334:724]. Down-regulation may also be obtained from the "sense" constructs by the phenomenon known as co-suppression [see Plant Cell 2:279–289; Plant Cell 2:291–299]. Tissue explants from plants are transformed using these vectors, subjected to selection for the presence of the integrated cassette, regenerated into plants [see Plant Cell Reports 8:325], and analyzed for altered expression of the PPO gene.

DESCRIPTION OF THE PREFERRED EMBODIMENTS

The following examples are provided for a more thorough understanding of the present invention. These examples are provided to demonstrate broad and various aspects of the present invention and are not meant to, nor should they be considered as to, limit the present invention to the specific conditions exhibited therein.

EXAMPLE I

Cloning of Polyphenol Oxidases

To clone PPO cDNAs by selection with antibodies, polyclonal antibodies were raised from purified PPO. A convenient source of PPO is *Solanum berthaultii* (wild potato) or *Lycopersicon esculentum* (tomato) which possess high densities of foliar glandular trichomes containing PPO as the dominant protein constituent (ca. 60%) of these organs [see J. Heredity 81:475]. PPO was obtained from foliar glandular trichomes of *Solanum berthaultii* by wiping leaflets (ca. 4000) with a cotton swab saturated in 200 mM dithiothreitol. The crude trichome extract was squeezed from the swab using a syringe, and centrifuged for 10 min at 12,000×g and 4° C. The supernatant was brought up to a volume of 30 ml with 2% pH 4–6 ampholyte and electrofocused in a preparative isoelectric focusing cell (Bio Rad Rotofor). Fractions from pH 4.5 to 6 were analyzed by electrophoresis on SDS-PAGE on a 10% polyacrylamide gel, followed by Coomassie staining to locate the protein. Fractions containing the purified 59 kD PPO were pooled and dialysed against two changes of 1 M NaCl (to remove ampholytes). The protein was then dialyzed against two changes of $H_2O$, and lyophilized. The purified, lyophilized PPO (300 μg) was reconstituted in 500 μl $H_2O$, emulsified with an equal volume of complete Freund's adjuvant, and injected into multiple subcutaneous sites on the back of two New Zealand White rabbits. Subsequent injections of 100 μg PPO in incomplete Freund's adjuvant were made at 15 and 21 d. The animals were exsanguinated and the antiserum collected 30 d after the final injection of PPO. Antiserum was stored at −80° C.

Specificity of the antibodies were demonstrated by immunoblotting SDS-PAGE or isoelectric focusing gels. Prior to transblotting to nitrocellulose membranes, gels were equilibrated 20 min in a transfer buffer of 25 mM Tris, 192 mM glycine, 20% (v/v) methanol, pH 8.3. Electrotransfer was accomplished at 100 V, 0.25 A for one hr. Non-specific binding to membranes was blocked, and the membranes washed, using conventional procedures [see Current Protocols in Molecular Biology (1987), ed F. M. Ausubel, John Wiley & Sons, New York; pp. 10.8.1–10.8.6]. Antibody was used at a dilution of 1:4000, and the blots were developed with goat anti-rabbit alkaline phosphatase conjugate and 5-bromo-4-chloro-3-indolyl phosphate, 367 mN nitroblue tetzazolium, 0.1M $NaHCO_3$, pH 9.8 [see Current Protocols in Molecular Biology (1987), ed F. M. Ausubel, John Wiley & Sons, New York; pp. 10.8.1–10.8.6]. When PPO from potato or tomato trichomes, leaves or other organs were electrophoresed on SDS-PAGE or isoelectric focusing gels, electroblotted onto nitrocellulose and probed with these polyclonal rabbit anti-PPO antibodies, the anti-PPO serum detected tomato and potato PPO equally well.

To obtain PPO mRNA for construction and screening of a cDNA expression library, mRNA was was obtained and verified to encode PPO. Forceps were used to peel 40 g of the epidermis and outer tissue layers from leaflets and petioles of tomato (*Lycopersicon esculentum* cv. VFNT Cherry). Peeled tissue was immediately frozen in liquid $N_2$. RNA was then extracted [see Analytical Biochemistry 162:156] and purified by oligo-dT cellulose column chromatography [see Molecular Cloning: A Laboratory Handbook, 2nd ed. (1989), ed. J. Sambrook, E. F. Fritsch, T. Maniatis, Cold Spring Harbor Laboratory Press; pp 197–198] to yield 30 μg polyadenylated RNA. 5 μg of the mRNA was translated in vitro in the presence of $^{35}S$-methionine using a reticulocyte lysate in vitro translation system (following the manufacturer's instructions [Promega Biotec]). The products of translation, when separated on 10% SDS-PAGE and autoradiographed overnight using Kodak XAR-5 film, did not clearly demonstrate the presence of the 59 kD PPO expected to be translated from mRNA of this tissue. Therefore, the translation products were subjected to immunoprecipitation. The translation reaction was diluted with nine volumes of 1% Nonidet P-40, 1% sodium deoxycholate, 0.1% SDS, 0.15 M NaCl, 1% methionine, 0.01 M sodium phosphate, ph 7.2. Twenty μl of 10% heat-killed *Staphlococcus aureus* cells was added to the translation mix and shaken at 4° C. for 1 h. The sample was then centrifuged at 13,000×g for five min. The supernatant was then incubated with 1 μl of anti-PPO antiserum at 4° C. overnight. Then 10 μl of 10% heat-killed *Staphlococcus aureus* cells was added and incubated at 4° C. for one h with intermittent shaking. After centrifugation at 13,000×g for five min the pellet was resuspended in 0.5 ml 1% Nonidet P-40, 1% sodium deoxycholate, 0.1% SDS, 0.15 M NaCl, 1% methionine, 0.01 M sodium phosphate, ph 7.2 and centrifuged three times through a 0.5 ml pad of 10% sucrose (in 0.5 ml 1% Nonidet P-40, 1% sodium deoxycholate, 0.1% SDS, 0.15 M NaCl, 1% methionine, 0.01 M sodium phosphate, ph 7.2) at 13,000×g for five min. The pellet was then washed three times with 0.5 ml 1% Nonidet P-40, 1% sodium deoxycholate, 0.1% SDS, 0.15 M NaCl, 1% methionine, 0.01 M sodium phosphate, ph 7.2. The immunoprecipiate (pellet) was then loaded onto 10% SDS-PAGE, electrophoresed, and autoradiographed overnight. This experiment showed that a product of 67 kD was precipitated by the anti-PPO. There was no evidence for a protein of 59 kD as would be expected from the $M_r$ of the PPO in the glandular trichome.

To determine whether the 67 kD protein immunoprecipitated was a precursor to the 59 kD PPO, a series of peptide mapping experiments were conducted using N-chlorsuccinimide and formic acid digestion [see Anal. Biochem. 122:298, and Anal. Biochem. 127:453]. Both N-chlorosuccinimide and formic acid were used to partially digest the mature 59 kD PPO from glandular trichomes and the $^{35}$S-labelled, immunoprecipitated 67 kD band from the in vitro translation. When the digestion products were electrophoresed, both the mature 59 kD PPO and the 67 kD translation product were found to share common fragment polypeptides. This result strongly suggested that the 59 kD PPO is initially translated as a 67 kD precursor polypeptide, and then processed proteolytically to its mature $M_r$ of 59,000.

A cDNA library was then constructed in λ ZAP (following the manufacturer's instructions [Stratagene]) using 2 µg polyadenylated tomato RNA, and was screened using a 1:4000 dilution of polyclonal anti-S. berthaultii PPO following conventional techniques [see Molecular Cloning: A Laboratory Handbook, pp 12.16–12.20; Methods of Enzymology, Vol. 152)]. After screening of 3×10⁵ plaques with PPO antibody, 12 candidates remained positive after quaternary screening. Restriction mapping of the candidate cDNAs showed that all 12 clones belonged to one of two different cDNA classes. Both classes of cDNA hybridized to bands of ca. 2.0 Kb on Northern blots [see Molecular Cloning: A Laboratory Handbook, pp 7.43–7.45] of tomato leaf and epidermal mRNA. The longest cDNA, however, was only 1.7 kbp, and a second screening of the library did not yield longer clones. A second λ ZAP II (Stratagene) cDNA library was therefore constructed using a new mRNA preparation. The library was screened, following conventional techniques (see Molecular Cloning: A Laboratory Handbook, pp 2.108–2.117, and the manufacturer's instructions), using a 0.7 kb truncated PPO cDNA obtained from the first library. After quaternary screening, two classes of PPO remained, (pPPO-T1 and pPPO-T2) both of a size approaching 2.0 kbp. Although both cDNAs hybridized with ca. 2.0 kb mRNA species on northern blots made from epidermal or leaf mRNA, northern blots conducted using tissue prints (see Plant Molecular Biology 12:517–524) of stem sections showed that pPPO-T1 is expressed in trichome and epidermal cells, and pPPO-T2 is expressed in photosynthetic cells.

The DNA sequence of tomato PPO cDNA pPPO-T1, according to the present invention, is as follows (Seq. ID 1):

```
ATG TCT TCT TCT TCT TCT ATT ACT ACT ACT CTT CCT TTA    39
TCC ACC AAC AAA TCC CTC TCT TCT TCC TTC ACC ACC ACC    78
AAC TCA TCC TTG TTA TCA AAA CCC TCT CAA CTT TTC CTC   117
CAC CGA AGG CGT AAT CAA AGT TTC AAG GTT TCA TGC AAC   156
GCA AAC AAC GTT GAC AAA AAC CCT GAC GCT GTT GAT AGA   195
CGA AAC GTT CTT TTA GGG TTA GGA GGT CTT TAT GGT GCA   234
GCT AAT CTT GCA CCA TTA GCG ACT GCT CGA CCT ATA CCA   273
CCT CCT GAT CTC AAG TCT TGT GGT ACT GCC CAT GTA AAA   312
GAA GGT GTT GAT GTA ATA TAC AGT TGT TGC CCT CCT GTA   351
CCC GAT GAG ATC GAT AGT GTT CCG TAC TAC AAG TTC CCT   390
TCT ATC ACT AAA CTC CGC ATC CGC CCC CCT GCT CAT GCG   429
GCG GAT GAG GAG TAC GTA GCC AAG TAT CAA TTG GCT ACG   468
AGT CGA ATG AGG GAA CTT GAT AAA GAC CCC TTT GAC CCT   507
CTT GGC TTT AAA CAA CAA GCT AAT ATT CAT TGT GCT TAT   546
TGC AAC GGT GCT TAC AAA GTT GGT GGT AAA GAA TTG CAA   585
GTT CAT TTC TCG TGG CTT TTC TTT CCC TTT CAT AGA TGG   624
TAC TTG TAC TTT TAC GAA AGA ATT TTG GGA TCA CTT ATT   663
AAT GAT CCA ACT TTT GCT TTA CCT TAC TGG AAT TGG GAT   702
CAT CCA AAA GGC ATG CGT ATA CCT CCC ATG TTT GAT CGT   741
GAG GGA TCA TCT CTT TAC GAT GAG AAA CGT AAC CAA AAT   780
```

```
CAT CGC AAT GGA ACT ATT ATT GAT CTT GGT CAT TTT GGT  819

AAG GAA GTT GAC ACA CCT CAG CTA CAG ATA ATG ACT AAT  858

AAT TTA ACC CTA ATG TAC CGT CAA ATG GTT ACT AAT GCT  897

CCT TGC CCT TCC CAA TTC TTC GGT GCT GCT TAC CCT CTG  936

GGT TCT GAA CCA AGT CCG GGT CAG GGT ACT ATT GAA AAC  975

ATC CCT CAT ACT CCG GTT CAC ATC TGG ACC GGT GAC AAA 1014

CCT CGT CAA AAA AAC GGT GAA GAC ATG GGT AAT TTC TAC 1053

TCA CCC GGT TTA GAT CCG ATT TTT TAC TGC CAC CAT GCC 1092

AAT GTG GAC AGG ATG TGG AAT GAA TGG AAA TTA ATT GGC 1131

GGG AAA AGA AGG GAT TTA ACA GAT AAA GAT TGG TTG AAC 1170

TCT GAA TTC TTT TTC TAC GAT GAA AAT CGT AAC CCT TAC 1209

CGT GTG AAG TCC GTA GAC TGT TTG GAC AGT AAA AAA ATG 1248

GGA TTC GAT TAC GCG CCA ATG CCC ACT CCA TGG CGT AAT 1287

TTT AAA CCA ATC AGA AAG TCA TCA TCA GGA AAA GTG AAT 1326

ACA GCG TCA ATT GCA CCA GTT AGC AAG GTG TTC CCA TTG 1365

GCG AAG CTG GAC CGT GCG ATT TCG TTC TCT ATC ACG CGG 1404

CCA GCC TCG TCA AGG ACA ACA CAA GAG AAA AAT GAG CAA 1443

GAG GAG ATA CTG ACA TTC AAT AAA ATA TCG TAT GAT GAT 1482

AGG AAC TAT GTA AGG TTC GAT GTG TTT CTG AAC GTG GAC 1521

AAG ACT GTG AAT GCA GAT GAG CTT GAT AAG GCG GAG TTT 1560

GCA GGG AGT TAT ACT AGC TTG CCG CAT GTT CAT GGA AGT 1599

AAT ACT AAT CAT GTT ACC AGT GTT ACT TTC AAG CTG GCG 1638

ATA ACT GAA CTG TTG GAG GAT ATT GGA TTG GAA GAT GAA 1677

GAT ACT ATT GCG GTG ACT TTG GTT CCA AAA GCT GGC GGT 1716

GAA GAA GTG TCC ATT GAA AGT GTG GAG ATC AAG CTT GAG 1755

GAT TGT                                              1761
```

In addition to the reading frame given above, the pPPO-T1 gene was sequenced with an upstream portion of the following sequence immediately prior to the ATG start codon (Seq. ID No. 2):

GGAATTCGGC ACGAGCTCCA TCACAACACA 30.

In addition to the upstream portion, a downstream portion was also sequenced according to the following (Seq. ID No. 3):

```
TAAAGTCTGC ATGAGTTGGT GGCTATGGTG CCAAATTTTA TGTTTAATTA  50
GTATAATTAT GTGTGGTTTG AGTTATGTTT TATGTTAAAA TGTATCAGCT 100
CGATCGATAG CTGATTGCTA GTTGTGTTAA TGCTATGTAT G          141
```

This cDNA sequence provides the following deduced amino acid sequence for the pPPO-T1 peptide (Seq. ID No 4):

```
Met Ser Ser Ser Ser Ile Thr Thr Thr Leu Pro Leu Cys Thr
                 5               10                  15
Asn Lys Ser Leu Ser Ser Phe Thr Thr Asn Ser Ser Leu
             20              25                  30
Leu Ser Lys Pro Ser Gln Leu Phe Leu His Gly Arg Arg Asn Gln
             35              40                  45
Ser Phe Lys Val Ser Cys Asn Ala Asn Val Asp Lys Asn Pro
             50              55                  60
Asp Ala Val Asp Arg Arg Asn Val Leu Leu Gly Leu Gly Leu
             65              70                  75
Tyr Gly Ala Ala Asn Leu Ala Pro Leu Ala Thr Ala Pro Ile
             80              85                  90
Pro Pro Pro Asp Leu Lys Ser Cys Gly Thr Ala His Val Lys Glu
             95             100                 105
Gly Val Asp Val Ile Tyr Ser Cys Cys Pro Pro Val Pro Asp Glu
            110             115                 120
Ile Asp Ser Val Pro Tyr Tyr Lys Phe Pro Ser Met Thr Lys Leu
            125             130                 135
Arg Ile Arg Pro Pro Ala His Ala Ala Asp Glu Glu Tyr Val Ala
            140             145                 150
Lys Tyr Gln Leu Ala Thr Ser Arg Met Arg Glu Leu Asp Lys Asp
            155             160                 165
Pro Phe Asp Pro Leu Gly Phe Lys Gln Gln Ala Asn Ile His Cys
            170             175                 180
Ala Tyr Cys Asn Gly Ala Tyr Lys Val Gly Gly Lys Glu Leu Gln
            185             190                 195
Val His Phe Ser Trp Leu Phe Phe Pro Phe His Arg Trp Tyr Leu
            200             205                 210
Tyr Phe Tyr Glu Arg Ile Leu Gly Ser Leu Ile Asn Asp Pro Thr
            215             220                 225
Phe Ala Leu Pro Tyr Trp Asn Trp Asp His Pro Lys Gly Met Arg
            230             235                 240
Ile Pro Pro Met Phe Asp Arg Glu Gly Ser Ser Leu Thr Asp Glu
            245             250                 255
Lys Arg Asn Gln Asn His Arg Asn Gly Thr Ile Ile Asp Leu Gly
            260             265                 270
His Phe Gly Lys Glu Val Asp Thr Pro Gln Leu Gln Ile Met Thr
            275             280                 285
Asn Asn Leu Thr Leu Met Tyr Arg Gln Met Val Thr Asn Ala Pro
            290             295                 300
Cys Pro Ser Gln Phe Phe Gly Ala Ala Tyr Pro Leu Gly Ser Glu
            305             310                 315
Pro Ser Pro Gly Gln Gly Thr Ile Glu Asn Ile Pro His Thr Pro
            320             325                 330
Val His Ile Trp Thr Gly Asp Lys Pro Arg Gln Lys Asn Gly Glu
            335             340                 345
Asp Met Gly Asn Phe Tyr Ser Pro Gly Leu Asp Pro Ile Phe Tyr
            350             355                 360
Cys His His Ala Asn Val Asp Arg Met Trp Asn Glu Trp Lys Leu
            365             370                 375
Ile Gly Gly Lys Arg Arg Asp Leu Thr Asp Lys Asp Trp Leu Asn
            380             385                 390
Ser Glu Phe Phe Phe Tyr Asp Glu Asn Arg Asn Pro Tyr Arg Val
            395             400                 405
```

-continued

```
Lys Ser Val Asp Cys Leu Asp Ser Lys Lys Met Gly Phe Asp Tyr
            410             415                 420
Ala Pro Met Pro Thr Pro Trp Arg Asn Phe Lys Pro Ile Arg Lys
            425             430                 435
Ser Ser Ser Gly Lys Val Asn Thr Ala Ser Ile Ala Pro Val Ser
            440             445                 450
Lys Val Phe Pro Leu Ala Lys Leu Asp Arg Ala Ile Ser Phe Ser
            455             460                 465
Ile Thr Arg Pro Ala Ser Ser Arg Thr Thr Gln Glu Lys Asn Glu
            470             475                 480
Gln Glu Glu Ile Leu Thr Phe Asn Lys Ile Ser Tyr Asp Asp Arg
            485             490                 495
Asn Tyr Val Arg Phe Asp Val Phe Leu Asn Val Asp Lys Thr Val
            500             505                 510
Asn Ala Asp Glu Leu Asp Lys Ala Glu Phe Ala Gly Ser Tyr Thr
            515             520                 525
Ser Leu Pro His Val His Gly Ser Asn Thr Asn His Val Thr Ser
            530             535                 540
Val Thr Phe Lys Leu Ala Ile Thr Glu Leu Leu Glu Asp Ile Gly
            545             550                 555
Leu Glu Asp Glu Asp Thr Ile Ala Val Thr Leu Val Pro Lys Ala
            560             565                 570
Gly Gly Glu Glu Val Ser Ile Glu Ser Val Glu Ile Lys Leu Glu
            575             580                 585
Asp Cys
    587
```

The pPPO-T1 cDNA was then subjected to in vitro transcription and translation to determine whether it was capable of encoding the 67 kD polypeptide expected for a cDNA encoding PPO. After linearization of the excised pBluescript-containing cDNAs with Xho I, RNA was transcribed using T3 RNA polymerase and capped (following the manufacturer's instructions [Stratagene]). The resulting pPPO-T1 mRNA (0.5 μg) was translated in vitro in the presence of $^{35}$S-methionine using a reticulocyte lysate in vitro translation system (see above). The products of translation were separated by SDS-PAGE on a 10% acrylamide gel. After electrophoresis the gel was dried and exposed for autoradiography overnight. The primary translation product was the 67 kD polypeptide shown earlier to be the precursor to the 59 kD mature PPO seen in immunoprecipitations of mRNA from the outer tissues of tomato foliage. Similar experiments were conducted with the tomato cDNA pPPO-T2.

The DNA sequence of tomato PPO cDNA pPPO-T2, according to the present invention, is as follows (Seq. ID No. 5):

```
ATG GCA AGT GTA GTG TGC AAT AGT AGT AGT AGT ACT ACT   39
ACT ACA ACG CTC AAA ACT CCT TTT ACT TCT TTA GGT TCC   78
ACT CCT AAG CCC TCT CAA CTT TTC CTT CAT GGA AAA CGT  117
AAC AAA ACA TTC AAA GTT TCA TGC AAG GTT ATC AAT AAT  156
AAC GGT AAC CAA GAT GAA ACG AAT TCT GTT GAT CGA AGG  195
AAT GTT CTT CTT GGT TTA GGA GGT CTT TAT GGT GTT GCT  234
AAT GCT ATA CCA TTA GCG GCA TCG GCT ACT CCT ATT CCA  273
TCC CCT GAT CTC AAA ACT TGT GGT AGA GCC ACC ATA TCG  312
GAT GGT CCA CTT GTA CCC TAT TCT TGT TGT CCC CCT CCT  351
ATG CCG ACT AAC TTT GAC ACC ATT CCA TAT TAC AAG TTC  390
CCT TCT ATG ACT AAA CTC CGT ATC CGT ACC CCT GCT CAT  429
```

-continued

```
GCT GTA GAT GAG GAG TAT ATC GCG AAG TAT AAT TTG GCC  468
ATA AGT CGA ATG AGG GAT CTT GAC AAG ACA GAA CCG TTA  507
AAC CCT CTA GGG TTT AAG CAA CAA GCT AAT ATA CAC TGT  546
GCT TAT TGT AAC GGT GCT TAT ATA ATT GGT GGC AAA GAG  585
TTA CAA GTT CAT AAC TCG TGG CTT TTC TTC CCG TTC CAT  624
CGA TGG TAC TTC TAC TTT TAC GAA AGA ATA TTG GGG AAA  663
CTC ATT GAT GAT CCA ACT TTC GCT TTA CCA TAC TGG AAT  702
TGG GAT CAT CCA AAG GGC ATG CGT TTA CCT CCC ATG TTC  741
GAT CGT GAA GGT TCT TCC CTC TAC GAT GAA AGG CGT AAT  780
CAA CAA GTC CGT AAT GGA ACG GTT TTG GAT CTT GGT TCA  819
TTT GGG GAT AAA GTT GAA ACA ACT CAA CTC CAG TTG ATG  858
AGC AAT AAT TTA ACC CTA ATG TAC CGT CAA ATG GTA ACT  897
AAT GCT CCA TGT CCT CTC TTG TTC TTC GGT GCG CCT TAC  936
GTT CTT GGG AAT AAC GTT GAA GCA CCG GGA ACC ATT GAA  975
ACC ATC CCT CAT ATT CCT GTA CAT ATT TGG GCT GGT ACT 1014
GTC CGT GGT TCA AAA TTT CCT AAC GGT GAT GTG TCC TAC 1053
GGT GAG GAT ATG GGT AAT TTC TAC TCA GCT GGT TTG GAC 1092
CCG GTT TTC TAT TGC CAT CAC GGC AAT GTG GAC CGG ATG 1131
TGG AAC GAA TGG AAG GCA ATA GGA GGT AAA AGA AGA GAT 1170
ATA TCT GAA AAG GAT TGG TTG AAC TCC GAG TTC TTT TTC 1209
TAC GAC GAA CAC AAA AAT CCT TAC CGT GTG AAA GTC AGG 1248
GAC TGT TTG GAC ACG AAG AAA ATG GGG TAT GAT TAC GCA 1287
CCA ATG CCA ACT CCA TGG CGT AAT TTC AAA CCA AAA TCA 1326
AAG GCG TCC GTA GGG AAA GTG AAT ACA AGT ACA CTC CCC 1365
CCA GCA AAC GAG GTA TTC CCA CTC GCG AAG ATG GAT AAG 1404
ACT ATT TCA TTT GCT ATC AAC AGG CCA GCT TCA TCG CGG 1443
ACT CAA CAA CAG AAA AAT GAA CAA GAG GAG ATG TTA ACG 1482
TTC AAT AAC ATA AGA TAT GAT AAC AGA GGG TAC ATA AGG 1521
TTG GAT GTG TTC CTG AAC GTG GAC AAC AAT GTG AAC GCG 1560
AAT GAG CTT GAT AAG GCA GAG TTC GCG GGG AGT TAT ACT 1599
AGT TTG CCA CAT GTT CAC AGA GCT GGC GAG AAT GAT CAT 1638
ATC GCG AAG GTT AAT TTC CAG CTG GCG ATA ACA GAA CTG 1677
TTG GAG GAC ATT GGT TTG GAA GAT GAA GAT ACT ATC GCG 1716
GTG ACT CTG GTA CCA AAG AAA GGC GGT GAA GGT ATC TCC 1755
ATT GAG AAT GTG GAG ATC AAG CTT GTG GAT TGT          1788
```

In addition to the reading frame given above, cDNA pPPO-T2 was sequenced with an upstream portion of the following sequence immediately prior to the ATG start codon (Seq. ID No. 6):

TAATTCGGCA CGAGAGCA 18

In addition to the upstream portion, a downstream portion was also sequenced according to the following (Seq ID No. 7):

```
TAAGTCTCAA TTGAATTTGC TGAGATTACA ATTATGATGG ATGATGATAT  50
GTTTTTATGT TACTTTTGTT CTGTTATCTA CTTTTGCTTT TCTCGTGTAA 100
CTTTTCCTGT TGAAATCACC CTACATGCTT GATTTCCTTG GAGTTGTTAT 150
TCACTAATAA ATCAGTTAGG TTAAAAAAAA AAAAAAAAA            189
```

This cDNA sequence provides the following deduced amino acid sequence for the pPPO-T2 peptide (Seq ID No. 8):

```
Met Ala Ser Val Val Cys Asn Ser Ser Ser Thr Thr Thr Thr
                  5                  10                  15

Thr Leu Lys Thr Pro Phe Thr Ser Leu Gly Ser Thr Pro Lys Pro
                 20                  25                  30

Ser Gln Leu Phe Leu His Gly Lys Arg Asn Lys Thr Phe Lys Val
                 35                  40                  45

Ser Cys Lys Val Ile Asn Asn Asn Gly Asn Gln Asp Glu Thr Asn
                 50                  55                  60

Ser Val Asp Arg Arg Asn Val Leu Leu Gly Leu Gly Gly Leu Tyr
                 65                  70                  75

Gly Val Ala Asn Ala Ile Pro Leu Ala Ala Ser Ala Thr Pro Ile
                 80                  85                  90

Pro Ser Pro Asp Leu Lys Thr Cys Gly Arg Ala Thr Ile Ser Asp
                 95                 100                 105

Gly Pro Leu Val Pro Tyr Ser Cys Cys Pro Pro Pro Met Pro Thr
                110                 115                 120

Asn Phe Asp Thr Ile Pro Tyr Tyr Lys Phe Pro Ser Met Thr Lys
                125                 130                 135

Leu Arg Ile Arg Thr Pro Ala His Ala Val Asp Glu Glu Tyr Ile
                140                 145                 150

Ala Lys Tyr Asn Leu Ala Ile Ser Arg Met Arg Asp Leu Asp Lys
                155                 160                 165

Thr Glu Pro Leu Asn Pro Leu Gly Phe Lys Gln Gln Ala Asn Ile
                170                 175                 180

His Cys Ala Tyr Cys Asn Gly Ala Tyr Ile Ile Gly Gly Lys Glu
                185                 190                 195

Leu Gln Val His Asn Ser Trp Leu Phe Phe Pro Phe His Arg Trp
                200                 205                 210

Tyr Phe Tyr Phe Tyr Glu Arg Ile Leu Gly Lys Leu Ile Asp Asp
                215                 220                 225

Pro Thr Phe Ala Leu Pro Tyr Trp Asn Trp Asp His Pro Lys Gly
                230                 235                 240

Met Arg Leu Pro Pro Met Phe Asp Arg Glu Gly Ser Ser Leu Tyr
                245                 250                 255

Asp Glu Arg Arg Asn Gln Gln Val Arg Asn Gly Thr Val Leu Asp
                260                 265                 270

Leu Gly Ser Phe Gly Asp Lys Val Glu Thr Thr Gln Leu Gln Leu
                275                 280                 285

Met Ser Asn Asn Leu Thr Leu Met Tyr Arg Gln Met Val Thr Asn
                290                 295                 300

Ala Pro Cys Pro Leu Leu Phe Phe Gly Ala Pro Tyr Val Leu Gly
                305                 310                 315

Asn Asn Val Glu Ala Pro Gly Thr Ile Glu Thr Ile Pro His Ile
```

```
                    -continued
              320              325              330

Pro Val His Ile Trp Ala Gly Thr Val Arg Gly Ser Lys Phe Pro
                335              340              345

Asn Gly Asp Val Ser Tyr Gly Glu Asp Met Gly Asn Phe Tyr Ser
                350              355              360

Ala Gly Leu Asp Pro Val Phe Tyr Cys His His Gly Asn Val Asp
                365              370              375

Arg Met Trp Asn Glu Trp Lys Ala Ile Gly Gly Lys Arg Arg Asp
                380              385              390

Ile Ser Glu Lys Asp Trp Leu Asn Ser Glu Phe Phe Phe Tyr Asp
                395              400              405

Glu His Lys Asn Pro Tyr Arg Val Lys Val Arg Asp Cys Leu Asp
                410              415              420

Thr Lys Lys Met Gly Tyr Asp Tyr Ala Pro Met Pro Thr Pro Trp
                425              430              435

Arg Asn Phe Lys Pro Lys Ser Lys Ala Ser Val Gly Lys Val Asn
                440              445              450

Thr Ser Thr Leu Pro Pro Ala Asn Glu Val Phe Pro Leu Ala Lys
                455              460              465

Met Asp Lys Thr Ile Ser Phe Ala Ile Asn Arg Pro Ala Ser Ser
                470              475              480

Arg Thr Gln Gln Glu Lys Asn Glu Gln Glu Glu Met Leu Thr Phe
                485              490              495

Asn Asn Ile Arg Tyr Asp Asn Arg Gly Tyr Ile Arg Phe Asp Val
                500              505              510

Phe Leu Asn Val Asp Asn Asn Val Asn Ala Asn Glu Leu Asp Lys
                515              520              525

Ala Glu Phe Ala Gly Ser Tyr Thr Ser Leu Pro His Val His Arg
                530              535              540

Ala Gly Glu Asn Asp His Ile Ala Lys Val Asn Phe Gln Leu Ala
                545              550              555

Ile Thr Glu Leu Leu Glu Asp Ile Gly Leu Glu Asp Glu Asp Thr
                560              565              570

Ile Ala Val Thr Leu Val Pro Lys Lys Gly Gly Glu Gly Ile Ser
                575              580              585

Ile Glu Asn Val Glu Ile Lys Leu Val Asp Cys
                590              595 596
```

The in vitro transcription/translation results from the pPPO-T2 cDNA was less clear, as it translated several products. This cDNA was later shown, by sequencing of its genomic counterpart, to be slightly less than full-length. Absence of a starting methionine codon in the cDNA apparently led to initiation of translation at downstream Met codons, accounting for the multiple PPO products.

The identification of the cDNA candidates as polyphenoloxidases was further confirmed by comparision of their deduced amino acid sequences to those obtained from sequencing PPO proteins from various sources. Glandular trichomes were harvested (see above) from foliage of *Lycopersicon esculentum* cv.s VFNT, Freedom, *Lycopersicon cheesmanii, L. chmielewskii,* and *Solanum berthaultii* by wiping leaves with a cotton swab saturated in 200 mM dithithreitol. The trichome extract was squeezed form the swab usning a syringe, and ⅒ volume of ice-cold trichloacetic acid was added to precipitate the proteins. The precipitate was suspended in 200 μl 0.5% SDS (w/v), 1.25% β-mercaptoethanol in 25 mM Tris, pH 7.5, and electrophoresed on a 10% SDS-PAGE gel system. After electrophoresis the gel was transblotted onto PVDF membrane (Immobilon-P) in 10 mM CAPS, pH 11, 10% MeOH. After transfer the membrane was stained with Coomassie Blue R-250 and destained. The PPO-containing bands, located by mol wt, were excised and the N-terminal amino acid sequence was obtained by microsequencing (see Guide to Protein Purification, e.d. M. P. Deutscher, Academic Press, San Diego; pp.602–613). The N-terminal sequences were as follows:

```
L. esculentum cv. VGNT (Seq. ID No. 9):
Ala Pro Ile Pro Pro Pro Asp Leu Lys Ser Gly Gly Thr Ala
                5                   10              14

L. esculentum cv. Freedom (SEQ ID NO: 10):

Ala Pro Ile Pro Pro Pro Asp Leu Lys Ser Asp Xaa Thr Ala
                5                   10              14

(Xaa = unable to assign residue)
L. cheesmanii (SEQ ID NO: 11):

Ala Pro Ile Pro Pro Pro Asp Leu Lys Ser Gln Gly Thr Ala His
                5                   10                  15

L. chmielewskii (SEQ ID NO: 12):

Ala Pro Ile Pro Pro Pro Asp Leu Lys Ser Gln Gly Thr Ala His
                5                   10                  15

S. berthaultii (SEQ ID NO: 13):

Ser Pro Ile Pro Pro Pro Asp Leu Lys Ser Xaa Gly Val Ala His
                5                   10                  15

Tyr Lys Glu Pro
        19
(Xaa = unable to assign residue)
```

The N-terminal amino acid sequence of the mature tomato (*L. esculentum* cv.VFNT) 59 kD PPO from glandular trichomes is also present within the deduced amino acid sequence of the pPPO-T1 cDNA. Similar deduced aminio acid sequence is present in the tomato cDNA pPPO-T2 and the potato cDNAs pPPO-P1 and pPPO-P2 (see below). The position of this sequence within the clones leads to deduced masses for the precursor protein and mature PPO polypeptide of ca. 67 and 59 kD, respectively. pPPO-T1 and pPPO-T2 show 78% nucleic acid sequence identity, and when compared over the length of the 67 kD precursor polypeptide possess 84% deduced amino acid similarity and 76% deduced amino acid identity. The genomic clones representing these cDNAs were recovered from a λ Ch35 library constructed from tomato (*Lycopersicon esculentum* cv. VFNT Cherry) and screened with tomato PPO cDNA, using conventional methods (see Molecular Cloning: A Laboratory Handbook, pp 2.108–2.113).

In addition, the 0.7 kb truncated tomato PPO cDNA was used to probe a potato leaf cDNA library, also constructed in λ ZAP II. Screening of $2 \times 10^5$ plaques led to the purification of three PPO cDNA candidates, two of which were about 2.0 Kbp in length, and a third truncated at about 1.2 Kbp. Northern analysis of a number of potato tissue explants including leaves, roots, flowers, tubers and petioles showed the presence of a single PPO class of 2.0 kb. DNA sequencing and comparison of the two longest potato PPO cDNAs (pPPO-P1 and pPPO-P2) showed 96% nucleic acid and deduced amino acid identity, and high sequence similarity to the tomato PPO cDNAs at both nucleic acid and deduced amino acid levels.

The DNA sequence of potato PPO cDNA pPPO-P1, according to the present invention, is as follows (Seq. ID No. 14):

```
TCT TCT TCT AGT ACT ACT ACT ATT CCA TTA TGC ACC AAC   39
AAA TCC CTC TCT TCT TCC TTC ACC ACC AAC AAC TCA TCT   78
TTC TTA TCA AAA CCC TCT CAA CTT TTC CTC CAC GGA AGG  117
CGT AAT CAA AGT TTC AAG GTT TCA TGC AAC GCC AAC AAT  156
AAT GTT GGC GAG CAT GAC AAA AAC CTT GAC ACT GTT GAT  195
AGG CGA AAT GTT CTT TTA GGG TTA GGA GGT CTT TAT GGT  234
GCT CCT AAT CTT GCA CCA TTA GCC TCT GCT TCT CCT ATA  273
CCA CCT CCT GAT CTA AAA TCT TGT GGT GTT GCC CAT GTA  312
ACA GAA GGT GTT GAT GTG ACA TAT AGT TGT TGC CCA CCT  351
GTA CCC GAT GAT ATC GAT AGC GTT CCG TAC TAC AAG TTC  390
CCT CCT ATG ACT AAA CTC CGC ATC CGC CCC CCT GCT CAT  429
GCG GCG GAT GAG GAG TAT GTA GCC AAG TAT CAA TTG GCT  468
```

-continued

```
ACG AGT CGA ATG AGG GAA CTT GAT AAA GAC TCT TTT GAC  507

CCT CTT GGG TTT AAA CAA CAA GCT AAT ATT CAT TGT GCT  546

TAT TGT AAC GGT GCT TAT AAA GTT GGT GGT AAA GAG TTG  585

CAA GTT CAT TTC TCG TGG CTT TTC TTT CCG TTT CAT AGA  624

TGG TAC TTG TAT TTC TAT GAA AGA ATA TTG GGA TCA CTT  663

ATT AAT GAT CCA ACT TTT GCT TTA CCA TAT TGG AAT TGG  702

GAT CAT CCA AAA GGT ATG CGT ATA CCT CCC ATG TTT GAT  741

CGT GAG GGG TCA TCT CTT TAC GAT GAT AAA CGT AAC CAA  780

AAC CAT CGC AAT GGA ACT ATT ATT GAT CTT GGT CAT TTT  819

GGT CAG GAA GTT GAC ACA CCT CAG CTT CAG ATA ATG ACT  858

AAT AAT TTA ACA CTA ATG TAC CGT CAA ATG GTC ACT AAT  897

GCT CCT TGT CCG TCC CAA TTC TTC GGT GCT GCT TAC CTC  936

TGG GGA CTG AAC CAA GTC CAG GAA TGG GTA CTA TTG AGA  975

ACA TCC CTC ATA CCC CGT GCC ATA TCT GGA CTG GTG ATA 1014

GTC CTA GAC AAA AAA ACG GTG AAA ACA TGG GTA ATT TCT 1053

ATT CAG CAC GGT TTA GAC CCG ATT TTT TAC TGT CAC CAC 1092

GCA AAT GTG GAC CGG ATG TGG GAT GAA TGG AAA TTA ATT 1131

GGC GGG AAA AGA AGG GAT CTA TCA AAT AAA GAT TGG TTG 1170

AAC TCA GAA TTC TTT TTC TAC GAT GAA AAT CGC AAC CCT 1209

TAC CGT GTG AAA GTC CGT GAC TGT TTG GAC AGT AAA AAA 1248

ATG GGA TTC AGT TAC GCT CCA ATG CCA ACT CCA TGG CGT 1287

AAT TTT AAA CCA ATC AGA AAA ACT ACA GCA GGA AAA GTG 1326

AAT ACA GCG TCA ATT GCA CCA GTC ACC AAG GTG TTC CCA 1365

CTA GCG AAG CTG GAC CGT GCA ATT TCG TTC TCT ATC ACC 1404

AGA CCA GCT TCG TCA AGG ACT ACA CAG GAG AAA AAT GAG 1443

CAA GAG GAG ATA CTG ACA TTC AAC AAA GTA GCC TAT GAT 1482

GAT ACT AAG TAT GTA AGG TTC GAT GTG TTC CTG AAC GTT 1521

GAC AAG ACT GTG AAT GCG GAT GAG CTT GAT AAG GCG GAG 1560

TTT GCG GGG AGT TAT ACT AGC TTG CCG CAT GTT CAT GGA 1599

AAT AAT ACT AAT CAT GTT ACG AGT GTT ACT TTC AAG CTG 1638

GCG ATA ACA GAA CTG TTG GAG GAT AAT GGA TTG GAA GAT 1677

GAA GAT ACT ATT GCG GTA ACT TTG GTT CCA AAA GTT GGT 1716

GGT GAA GGT GTA TCC ATT GAA AGT GTG GAG ATC AAG CTT 1755

GAG GAT TGT                                         1764
```

In addition, a downstream portion was also sequenced according to the following (Seq. ID No. 15):

```
TAAGTCCTCA TGAGTTGGTG GCTATGGTAC CAAATTTTAT GTTTAATTAT  50

ATTAATGTGT GTGTTTGATT ATGTTTCGGT TAAAATGTAT CAGCTGGATA 100

GCTGATTACT AGCCTTCCCA GTTGTTAATG CTATGTATGA AATAAATAAA 150
```

-continued

```
TAAATGGTTG TCTTCCATTT AATTTTAAAA AAAAAAAAAA AAAAAAAAAA    200

AAAAAAAAAA AAAAAAAAAA AA                                  222
```

This cDNA sequence provides the following deduced amino acid sequence for the pPPO-P1 peptide (Seq. ID No. 16):

```
Ser Ser Ser Ser Thr Thr Thr Ile Pro Leu Tyr Thr Asn Lys Ser
                5               10              15

Leu Ser Ser Ser Phe Thr Thr Asn Asn Ser Ser Phe Leu Ser Lys
                20              25              30

Pro Ser Gln Leu Phe Leu His Gly Arg Arg Asn Gln Ser Phe Lys
                35              40              45

Val Ser Tyr Asn Ala Asn Asn Asn Val Gly Glu His Asp Lys Asn
                50              55              60

Leu Asp Thr Val Asp Arg Arg Asn Val Leu Leu Gly Leu Gly Gly
                65              70              75

Leu Tyr Gly Ala Ala Asn Leu Ala Pro Leu Ala Ser Ala Ser Pro
                80              85              90

Ile Pro Pro Pro Asp Leu Lys Ser Gys Gly Val Ala His Val Thr
                95              100             105

Glu Gly Val Asp Val Thr Tyr Ser Cys Try Pro Pro Val Pro Asp
                110             115             120

Asp Ile Asp Ser Val Pro Tyr Tyr Lys Phe Pro Pro Met Thr Lys
                125             130             135

Leu Arg Ile Arg Pro Pro Ala His Ala Ala Asp Glu Glu Tyr Val
                140             145             150

Ala Lys Tyr Gln Leu Ala Thr Ser Arg Met Arg Glu Leu Asp Lys
                155             160             165

Asp Ser Phe Asp Pro Ieu Gly Phe Lys Gln Gln Ala Asn Ile His
                170             175             180

Cys Ala Tyr Cys Asn Gly Ala Try Lys Val Gly Gly Lys Glu Leu
                185             190             195

Gln Val His Phe Ser Trp Leu Phe Phe Pro Phe His Arg Trp Tyr
                200             205             210

Leu Try Phe Tyr Glu Arg Ile Leu Gly Ser Leu Ile Asn Asp Pro
                215             220             225

Thr Phe Ala Leu Pro Tyr Trp Asn Trp Asp His Pro Lys Gly Met
                230             235             240

Arg Ile Pro Pro Met Phe Asp Arg Glu Gly Ser Ser Leu Tyr Asp
                245             250             255

Asp Lys Arg Asn Gln Asn His Arg Asn Gly Thr Ile Ile Asp Leu
                260             265             270

Gly His Phe Gly Gln Glu Val Asp Thr Pro Gln Leu Gln Ile Met
                275             280             285

Thr Asn Asn Leu Thr Leu Met Tyr Arg Gln Met Val Thr Asn Ala
                290             295             300

Pro Cys Pro Ser Gln Phe Phe Gly Ala Ala Tyr Leu Trp Gly Leu
                305             310             315

Asn Gln Val Gln Glu Trp Val Leu Leu Arg Thr Ser Leu Ile Pro
                320             325             330

Arg Ala Ile Ser Gly Leu Val Ile Val Leu Asp Lys Lys Thr Val
```

```
                        335                340                345
Lys Thr Trp Val Ile Ser Ile Gln His Gly Leu Asp Pro Ile Phe
                350                355                360

Tyr Cys His His Ala Asn Val Asp Arg Met Trp Asp Glu Trp Lys
                365                370                375

Leu Ile Gly Gly Lys Arg Arg Asp Leu Ser Asn Lys Asp Trp Leu
                380                385                390

Asn Ser Glu Phe Phe Phe Tyr Asp Glu Asn Arg Asn Pro Tyr Arg
                395                400                405

Val Lys Val Arg Asp Gys Leu Asp Ser Lys Lys Met Gly Phe Ser
                410                415                420

Tyr Ala Pro Met Pro Thr Pro Trp Arg Asn Phe Lys Pro Ile Arg
                425                430                435

Lys Thr Thr Ala Gly Lys Val Asn Thr Ala Ser Ile Ala Pro Val
                440                445                450

Thr Lys Val Phe Pro Leu Ala Lys Leu Asp Arg Ala Ile Ser Phe
                455                460                465

Ser Ile Thr Arg Pro Ala Ser Ser Arg Thr Thr Gln Glu Lys Asn
                470                475                480

Glu Gln Glu Glu Ile Leu Thr Phe Asn Lys Val Ala Tyr Asp Asp
                485                490                495

Thr Lys Tyr Val Arg Phe Asp Val Phe Leu Asn Val Asp Lys Thr
                500                505                510

Val Asn Ala Asp Glu Leu Asp Lys Ala Glu Phe Ala Gly Ser Tyr
                515                520                525

Thr Ser Leu Pro His Val His Gly Asn Asn Thr Asn His Val Thr
                530                535                540

Ser Val Thr Phe Lys Leu Ala Ile Thr Glu Leu Leu Glu Asp Asn
                545                550                555

Gly Leu Glu Asp Glu Asp Thr Ile Ala Val Thr Leu Val Pro Lys
                560                565                570

Val Gly Gly Glu Gly Val Ser Ile Glu Ser Val Glu Ile Lys Leu
                575                580                585

Glu Asp Cys
        588
```

The DNA sequence of tomato PPO cDNA pPPO-P2, according to the present invention, is as follows (Seq. ID No. 17):

```
ACT ACT CTT CCA TTA TGC AAC AAC AAA TCC CTC TCT TCT    39

TCC TTC ACC ACC AAC AAC TCA TCT TTC TTA TCA AAA CCC    78

TCT CAA CTT TTC CTC CAC GGA AGG CGT AAT CAA AGT TTC    117

AAG GTT TCA TGC AAC GCC AAC AAT AAT GTT GGC GAG CAT    156

GAC AAA AAC CTT GAC GCT GTT GAT AGG CGA AAT GTT CTT    195

TTA GGG TTA GGA GGT CTT TAT GGT GCT GCT AAT CTT GCA    234

CCA TTA GCC TCT GCT TCT CCT ATA CCA CCT CCT GAT CTA    273

AAA TCT TGT GGT GTT GCC CAT GTA AAA GAA GGT GTT GAT    312

GTG TCA TAC AGT TGT TGC CCT CCT GTA CCC GAT GAT ATC    351

GAT AGC GTT CCG TAC TAC AAG TTC CCT TCT ATG ACT AAA    390
```

```
CTC CGC ATC CGC CCC CCT GCT CAT GCG GCG GAT GAG GAG    429
TAT GTA GCC AAG TAT CAA TTG GCT ACG AGT CGA ATG AGG    468
GAA CTT GAT AAA GAC TCT TTT GAC CCT CTT GGG TTT AAA    507
CAA CAA GCT AAT ATT CAT TGT GCT TAT TGT AAC GGT GCT    546
TAT AAA GTT GGT GGT AAA GAG TTG CAA GTT CAT TTC TCG    585
TGG CTT TTC TTT CCG TTT CAT AGA TGG TAC TTG TAC TTC    624
TAC GAA AGA ATT TTG GGA TCA CTT ATT AAT GAT CCA ACT    663
TTT GCT TTA CCA TAT TGG AAT TGG GAT CAT CCA AAA GGT    702
ATG CGT ATA CCT CCC ATG TTT GAT CGT GAG GGG TCA TCT    741
CTT TAC GAT GAT AAA CGT AAC CAA AAC CAT CGC AAT GGA    780
ACT ATT ATT GAT CTT GGT CAT TTT GGT AAG GAA GTT GAC    819
ACA CCT CAG CTC CAG ATA ATG ACT AAT AAT TTA ACA CTA    858
ATG TAC CGT CAA ATG GTC ACT AAT GCT CCT TGT CCG TCC    897
CAA TTC TTC GGT GCT GCT TAC CTC TGG GGA CTG AAC CAA    936
GTC CGG GAC AGG GTA CTA TTG AGA ACA TCC CTC ATA CTC    975
CGG TTC ACA TCT GGA CCG GTG ACA AAC CTC GAC AAA AAA   1014
ACG GTG AAA ACA TGG GTA ATT TCT ATT CAG CAC GGT TTA   1053
GAC CCG CTT TTT TAC TGT CAC CAT GCA AAT GTG GAC CGG   1092
ATG TGG GAT GAA TGG AAA TTA ATT GGT GGG AAA AGA AGG   1131
GAT CTA TCA AAT AAA GAT TGG TTG AAC TCA GAA TTC TTT   1170
TTC TAC GAT GAA AAT CGC AAC CCT TAC CGT GTG AAA GTC   1209
CGT GAC AGT TTG GAC AGT AAA AAA ATG GGA TTC AGT TAC   1248
GCT CCA ATG CCA ACT CCA TGG CGT AAT TTT AAA CCA ATC   1287
AGA AAA ACT ACA GCA GGA ATA GTG AAT ACA GCG TCA ATT   1326
GCA CCA GTC ACC AAG GTG TTC CCA CTG GCG AAG CTG GAC   1365
CGT GCG ATT TCA TTC TCT ATC ACC AGA CCA GCT TCG TCA   1404
AGG ACT ACG CAG GAG AAA AAT GAG GAA GAG GAG ATA CTG   1443
ACA TTC AAA AAG ATA GCC TAT GAT GAT ACT CAG TAT GTA   1482
AGG TTC GAT GTG TTC CTG AAC GTT GAC AAG ACT GTG AAT   1521
GCG GAT GAG CTT GAT AAG GCA GAG TTT GCG GGG AGT TAT   1560
ACT AGC TTG CCG CAT GTT CAT GGA AAT AAT ACT AAT CAT   1599
GCT ACG AGT GTT ACT TTC ACA GCT GGC ATA ACA GAA CTG   1638
TTG GAG GAT ATT GGA TTG GAA GAT GAA GAT ACT ATT GCG   1677
GTA ACT TTG GTT CCA AAA GTA GGT GGT GAA GGT GTA TCC   1716
ATT GAA AGT GTG GAG ATC AAG CTT GAG GAT TGT          1749
```

In addition, a downstream portion was also sequenced according to the following (Seq. ID No. 18):

```
TAAGTCCTCA TGAGTTGGTG GCTATGGTAC CAAATTTTAT GTTTAATTAG    50

TATTAATGTG TGTATGTGTT GATTATGTTT CGGGTAAAAT GTATCAGCTG   100

GATAGCTGAT TACTAGCCTT GCCAGTTGTT AATGCTATGT ATGAAATAAA   150

TAAATAAAAA AAAAAAAAAA AAA    173
```

This cDNA sequence provides the following deduced amino acid sequence for the pPPO-P2 peptide (Seq. ID No. 19):

```
Thr Thr Leu Pro Leu Cys Asn Asn Lys Ser Leu Ser Ser Ser Phe
                 5                  10                  15

Thr Thr Asn Asn Ser Ser Phe Leu Ser Lys Pro Ser Gln Leu Phe
                20                  25                  30

Leu His Gly Arg Arg Asn Gln Ser Phe Lys Val Ser Cys Asn Ala
                35                  40                  45

Asn Asn Asn Val Gly Glu His Asp Lys Asn Leu Asp Ala Val Asp
                50                  55                  60

Arg Arg Asn Val Leu Leu Gly Leu Gly Leu Tyr Gly Ala Ala
                65                  70                  75

Asn Leu Ala Pro Leu Ala Ser Ala Ser Pro Ile Pro Pro Asp
                80                  85                  90

Leu Lys Ser Cys Gly Val Ala His Val Lys Glu Gly Val Asp Val
                95                 100                 105

Ser Tyr Ser Cys Cys Pro Pro Val Pro Asp Asp Ile Asp Ser Val
               110                 115                 120

Pro Tyr Tyr Lys Phe Pro Ser Met Thr Lys Leu Arg Ile Arg Pro
               125                 130                 135

Pro Ala His Ala Ala Asp Glu Glu Tyr Val Ala Lys Tyr Gln Leu
               140                 145                 150

Ala Thr Ser Arg Met Arg Glu Leu Asp Lys Asp Ser Phe Asp Pro
               155                 160                 165

Leu Gly Phe Lys Gln Gln Ala Asn Ile His Gys Ala Tyr Cys Asn
               170                 175                 180

Gly Ala Tyr Lys Val Gly Gly Lys Glu Leu Gln Val His Phe Ser
               185                 190                 195

Trp Leu Phe Phe Pro Phe His Arg Trp Tyr Leu Tyr Phe Tyr Glu
               200                 205                 210

Arg Ile Leu Gly Ser Leu Ile Asn Asp Pro Thr Phe Ala Leu Pro
               215                 220                 225

Tyr Trp Asn Trp Asp His Pro Lys Gly Met Arg Ile Pro Pro Met
               230                 235                 240

Phe Asp Arg Glu Gly Ser Ser Leu Tyr Asp Asp Lys Arg Asn Gln
               245                 250                 255

Asn His Arg Asn Gly Thr Ile Ile Asp Leu Gly His Phe Gly Lys
               260                 265                 270

Glu Val Asp Thr Pro Gln Leu Gln Ile Met Thr Asn Asn Leu Thr
               275                 280                 285

Leu Met Tyr Arg Gln Met Val Thr Asn Ala Pro Cys Pro Ser Gln
               290                 295                 300

Phe Phe Gly Ala Ala Tyr Leu Trp Gly Leu Asn Gln Val Arg Asp
               305                 310                 315

Arg Val Leu Leu Arg Thr Ser Leu Ile Leu Arg Phe Thr Ser Gly
```

```
                    -continued
              320             325             330
Pro Val Thr Asn Leu Asp Lys Lys Thr Val Lys Thr Trp Val Ile
            335             340             345

Ser Ile Gln His Gly Leu Asp Pro Leu Phe Tyr Cys His His Ala
            350             355             360

Asn Val Asp Arg Met Trp Asp Glu Trp Lys Leu Ile Gly Gly Lys
            365             370             375

Arg Arg Asp Leu Ser Asn Lys Asp Trp Leu Asn Ser Glu Phe Phe
            380             385             390

Phe Tyr Asp Glu Asn Arg Asn Pro Tyr Arg Val Lys Val Arg Asp
            395             400             405

Ser Leu Asp Ser Lys Lys Met Gly Phe Ser Tyr Ala Pro Met Pro
            410             415             420

Thr Pro Trp Arg Asn Phe Lys Pro Ile Arg Lys Thr Thr Ala Gly
            425             430             435

Ile Val Asn Thr Ala Ser Ile Ala Pro Val Thr Lys Val Phe Pro
            440             445             450

Leu Ala Lys Leu Asp Arg Ala Ile Ser Phe Ser Ile Thr Arg Pro
            455             460             465

Ala Ser Ser Arg Thr Thr Gln Glu Lys Asn Glu Gln Glu Glu Ile
            470             475             480

Leu Thr Phe Lys Lys Ile Ala Tyr Asp Asp Thr Gln Tyr Val Arg
            485             490             495

Phe Asp Val Phe Leu Asn Val Asp Lys Thr Val Asn Ala Asp Glu
            500             505             510

Leu Asp Lys Ala Glu Phe Ala Gly Ser Tyr Thr Ser Leu Pro His
            515             520             525

Val His Gly Asn Asn Thr Asn His Ala Thr Ser Val Thr Phe Thr
            530             535             540

Ala Gly Ile Thr Glu Leu Leu Glu Asp Ile Gly Leu Glu Asp Glu
            545             550             555

Asp Thr Ile Ala Val Thr Leu Val Pro Lys Val Gly Gly Glu Gly
            560             565             570

Val Ser Ile Glu Ser Val Glu Ile Lys Leu Glu Asp Cys
            575             580         583
```

The sequence for pPPO-T1 given above includes several bp determined from sequencing its genomic clone. In both tomato and potato all PPO cDNAs map to chromosome 8. PPOs are encoded by a family of genes which typically specify the synthesis of precursor proteins of $M_r$ ca. 67,000 which are then processed to a mature $M_r$ of ca. 59,000. A number of posttranslational modification events such as crosslinking via quinones, glycosylation, and proteolysis (see Phytochemistry 18: 193–215, and Phytochemistry 26: 11–20) gives rise to multiple $M_r$ and pI species observed for mature PPOs.

EXAMPLE II

Transformation of Potato to Achieve Altered PPO Expression

The potato PPO cDNA (pPPO-P1) was excised from pBluescipt using Sma I and Xho I. The resulting 5' overhang from the Xho I restriction digest was filled in using the Klenow fragment of DNA Pol I. The transformation construct pBI121 was restriction digested with Sma I and Sst I. The resulting 3' overhang was treated with T4 DNA polymerase to produce a blunt end. This procedure removed the endogenous GUS gene and prepared the vector for pPPO-1 integration. The PPO insert and pBI121 prepared as described above were ligated overnight using T4 DNA ligase in a reaction employing a 2:1 ratio of insert to vector. The resulting recombinant pBI121/PPO plasmids were electroporated into *E. coli* strain DH5a. Plasmid was isolated from $kan^r$ colonies and restriction digested with Bam HI/Kpn I, and Bam HI/Pst I, to positively identify sense and antisense constructs, respectively. For both constructs, HindIII/Xba I restriction digests were carried out to confirm the integrity of the CaMV 35S promoter of the vector.

Sense and antisense PPO-containing plasmids were electroporated into *Agrobacterium tumefaciens* (PC2760) (Nucleic Acids Research 16:6127–6145; Molecular and General Genetics 216:175–177; Nucleic Acids Research 17:6747). Microtuber discs of potato (*Solanum tuberosum* L. cv. Atlantic) were inoculated for 15 min and then co-cultivated for two days with Agrobacterium cultures harboring either the pPPO-P1 sense or antisense constructs and then transferred to medium containing kanamycin. Plantlets regenerating from the tuber discs were removed and transferred to larger containers for growth (see Plant Cell Reports 8:325–328).

To determine endogenous PPO levels, leaf samples of non-transformed potato plants were homogenized in buffer containing 1.25% b-mercaptoethanol and 0.5% SDS, boiled for 5 min, and loaded on 10% SDS-PAGE. Following electrophoresis, gels were electroblotted onto nitrocellulose and probed with polyclonal rabbit anti-PPO antibodies (see above), then developed with goat anti-rabbit alkaline phosphatase conjugate. Similar leaf extracts were made from regenerated plants transformed with the sense and antisense PPO constructs. Equal amounts of protein from non-transformed, PPO transformants and control plants (transformed with pBI121 alone) were loaded in each well of the SDS-PAGE gels. After electrotransfer and immunoblotting with polyclonal rabbit anti-PPO antibodies as described above, the results showed that those plants transformed with constructs containing PPO in either sense or antisense orientations possessed a range of altered PPO expression relative to non-transformed plants or control transformed with the pBI121 vector alone. The range of expression present in transformed plants was from several fold overexpression to nearly undetectable levels of PPO.

EXAMPLE III

Transformation of Tomato With Antisense PPO Constructs to Achieve Decreased PPO Expression The potato PPO cDNA (pPPO-P1) was excised from pBluescript using Sma I and Xho I. The resulting 5' overhang from the Xho I restriction digest was filled in using the Klenow fragment of DNA Pol I. The transformation construct pBI121 was restriction digested with Sma I and Sst I. The resulting 3' overhang was treated with T4 DNA polymerase to produce a blunt end. This procedure removed the endogenous GUS gene and prepared the vector for pPPO-P1 integration. The PPO insert and pBI121 prepared as described above were ligated overnight using T4 DNA ligase in a reaction employing a 2:1 ratio of insert to vector. The resulting recombinant pBI121/PPO plasmids were electroporated into E. coli strain DH5a. Plasmid was isolated from kanr colonies and restriction digested with Bam HI/Kpn I and Bam HI/Pst I to positively identify sense and antisense constructs, respectively. For both constructs, Hind III/Xba I restriction digests were carried out to confirm the integrity of the CaMV 35S promoter.

Antisense PPO-containing plasmids were electroporated into Agobacterium tumefaciens (LBA4404) (see Gene 90:149; Plasmid 7:15). Hypocotyl and cotyledon explants of tomato (Lycopersicon esculentum cv. Moneymaker) were inoculated for 10 min and then co-cultivated for four days with Agrobacterium cultures harboring the pPPO-P1 antisense constructs and then transferred to selective medium containing kanamycin. Plantlets regenerating from the explants were removed and transferred to selective rooting medium (see Plant Molec. Biol. Rep. 1:88).

After transfer from tissue culture to the greenhouse, DNA of the plants was analyzed to confirm that they were transformed. Genomic DNA was isolated from leaves, restriction digested with EcoR1 and probed with a $^{32}$P-radiolabelled probe made from the NPT-II gene which lies 5' to the PPO insert in the transformation vector, using the Southern hybridization procedure (see Molecular Cloning: A Laboratory handbook, 2nd ed. (1989), ed. J. Sambrook, E. F. Fritsch, T. Maniatis, cold Spring Harbor Laboratory Press; pp 9.31–9.57).

Seventeen tomato plants were confirmed to be transformed by this procedure. To determine the effect of antisense expression on PPO levels, leaf samples of antisense transformants and plants transformed with pBI121 alone were analyzed by immunoblotting with PPO antibody. Leaf samples were homogenized in 0.1 M Tris-HCl pH 7, 3% (w/v) polyvinylpolypyrrolidone, 0.1M KCl, 1 mM phenylmethylsulfonylfluoride, 1 mg/ml leupeptin, 5 mg/ml chymostatin, 1% (v/v) Triton X-100, 1 mM $Na_2$ EDTA, boiled for 5 min in 1× Laemmli buffer (see Nature 227:680). Equal amounts of protein of all samples were loaded and separated by 10% SDS-polyacrylamide gel electrophoresis. Duplicate samples were run on a separate gel and stained with Coomassie blue to confirm equal loading of each sample.

The unstained gel was transblotted to nitrocellulose membranes after 10 min equilibration in a transfer buffer of 25 mM Tris, 192 mM glycine, 20% (v/v) methanol, pH 8.3. Electrotransfer was accomplished at 100 V, 0.25 A for 20 min. Membranes were treated with NaIO4 (3% w/v) for 10 min to remove non-specific glycosidic epitopes, blocked in 1% (w/v) dry milk, and washed, using conventional procedures (see Current Protocols in Molecular Biology (1987), ed F. M. Ausubel, John Wiley & Sons, New York; pp. 10.8.1–10.8.6). Antibody was used at a dilution of 1:1000, and the blots were developed with goat anti-rabbit alkaline phosphatase conjugate and 5-bromo-4-chloro-3-indolyl phosphate, 367 mN nitroblue tetrazolium, 0.1M $NaHCO_3$, pH 9.8 (see Current Protocols in Molecular Biology (1987), ed F. M. Ausubel, John Wiley & Sons, New York; pp. 10.8.1–10.8.6).

Of the seventeen tomato plants analyzed, eleven exhibited no change in the level of PPO expression when compared to control plants. Two antisense transformants (plants #88-3, 88-8) possessed slightly lower amounts of PPO than the controls. Three antisense transformants (plants #19-8, 19-9, 88-1) had nearly undetectable levels of PPO. One antisense transformant (#19-4) showed a complete absence of immunologically detectable PPO.

PPO activity (see Anal. Biochem. 77:486) was then determined for the control tomato plants and for the five tomato plants shown by immunoblotting to possess greatly decreased PPO expression. Plants were grown in the greenhouse under supplemental lighting (16 hr photoperiod) and leaflets from the first or second apical node were analyzed. The controls (plants NT-1 and NT-2 exhibited PPO activity of 647 and 927 mmol quinone formed/min/mg protein, respectively. Transformed plant #19-9 possessed PPO activity of 114 mmol quinone formed/min/mg protein, whereas PPO activity was undetectable in plants 19-8 and 88-1. PPO activity was also not detected in plant 19-4 which had no detectable PPO by immunoblotting.

EXAMPLE IV

Overproduction of PPO Via Sense Constructs

The tomato PPO gene pPPO-T1 was used to construct a transformation vector possessing the CaMV 35S promoter controlling PPO expression in the sense orientation. This construct was then used to transform tobacco (Nicotiana tabacum cv Petite havana) to achieve increased expression of PPO.

Tobacco leaf strips were dipped into a solution containing a 1:10 dilution of an overnight culture of Agrobacterium tumefaciens (LBA4404) and then cocultivated for two days before transferring to kanamycin and regeneration (see Plant Molecular Biology Manual A5:1, Kluwer Academic Publishers, Dordrecht).

After transfer from tissue culture to the greenhouse, DNA of the plants was analyzed to confirm that they were transformed. Genomic DNA was isolated from leaves, restriction digested with EcoR1 and probed with a $^{32}$P-radiolabelled probe made from the NPT-II gene which lies 5' to the PPO insert in the transformation vector, using the Southern hybridization procedure (see Molecular Cloning: A Laboratory handbook, 2nd ed. (1989), ed. J. Sambrook, E. F. Fritsch, T. Maniatis, cold Spring Harbor Laboratory Press; pp 9.31–9.57).

Twenty transformed tobacco plants were obtained by this procedure. To determine the effect of sense expression on PPO levels, leaf samples of the pBl121:PPO transformants as well as tobacco plants transformed with pBl121 alone were analyzed by immunoblotting with PPO antibody. Leaf samples were homogenized in 0.1M Tris-HCl pH 7, 3% (w/v) polyvinylpolypyrrolidone, 0.1 M KCl, 1 mM phenylmethylsulfonylfluoride, 1 mg/ml leupeptin, 5 mg/ml chymostatin, 1% (v/v) Triton X-100, 1 mM $Na_2$ EDTA, boiled for 5 min in 1× Laemmli buffer (see Nature 227:680). Equal amounts of protein of all samples were loaded and separated by 10% SDS-polyacrylamide gel electrophoresis. Duplicate samples were run on a separate gel and stained with Coomassie blue to confirm equal loading of each sample.

The unstained gel was transblotted to nitrocellulose membranes after 10 min equilibration in a transfer buffer of 25 mM Tris, 192 mM glycine, 20% (v/v) methanol, pH 8.3. Electrotransfer was accomplished at 100 V, 0.25 A for 20 min. Membranes were treated with NaIO4 (3% w/v) for 10 min to remove non-specific glycosidic epitopes, blocked in 1% (w/v) dry milk, and washed, using conventional procedures (see Current Protocols in Molecular Biology (1987), ed F. M. Ausubel, John Wiley & Sons, New York; pp. 10.8.1–10.8.6). Antibody was used at a dilution of 1:1000, and the blots were developed with goat anti-rabbit alkaline phosphatase conjugate and 5-bromo-4-chloro-3-indolyl phosphate, 367 mN nitroblue tetrazolium, 0.1M $NaHCO_3$, pH 9.8 (see Current Protocols in Molecular Biology (1987), ed F. M. Ausubel, John Wiley & Sons, New York; pp. 10.8.1–10.8.6).

Of the twenty transformed tobacco plants analyzed by immunoblotting, six had no change in PPO level. Four exhibited slightly decreased PPO level relative to the control plants, and two had nearly undetectable levels of PPO. Seven had increased PPO levels, and one had much higher levels of PPO expression than the control plants. In all cases the overexpressed PPO possessed the expected molecular weight of 59,000.

The eight plants exhibiting increased levels of leaf PPO were allowed to flower, self-fertilize and set seed. The selfed seed was harvested and allowed to germinate on agar containing 300 mg/ml kanamycin to select for transgenic progeny (see Plant Molecular Biology Manual A5:1, Kluwer Academic Publishers, Dordrecht). Surviving transgenic seedlings were then transferred to soil and grown under artificial lighting (16 h photoperiod) at ca. 25° C. Three weeks later, leaves of the progeny and nontransformed controls were compared for leaf PPO by immunoblotting. Leaf samples (3 to 4 nodes from the apex) were harvested and protein homogenized in in 0.1 M Tris-HCl pH 7, 3% (w/v) polyvinylpolypyrrolidone, 0.1M KCl, 1 mM phenylmethylsulfonylfluoride, 1 mg/ml leupeptin, 5 mg/ml chymostatin, 1% (v/v) Triton X-100, 1 mM $Na_2$ EDTA, boiled for 5 min in 1× Laemmli buffer (see Nature 227:680). Equal amounts of protein of all samples were loaded and separated by 10% SDS-polyacrylamide gel electrophoresis. Duplicate samples were run on a separate gel and stained with Coomassie blue to confirm equal loading of each sample.

The unstained gel was transblotted to nitrocellulose membranes after 10 min equilibration in a transfer buffer of 25 mM Tris, 192 mM glycine, 20% (v/v) methanol, pH 8.3. Electrotransfer was accomplished at 100 V, 0.25 A for 20 min. Membranes were treated with NaIO4 (3% w/v) for 10 min to remove non-specific glycosidic epitopes, blocked in 1% (w/v) dry milk, and washed, using conventional procedures (see Current Protocols in Molecular Biology (1987), ed F. M. Ausubel, John Wiley & Sons, New York; pp. 10.8.1–10.8.6). Antibody was used at a dilution of 1:1000, and the blots were developed with goat anti-rabbit alkaline phosphatase conjugate and 5-bromo-4-chloro-3-indolyl phosphate, 367 mN nitroblue tetrazolium, 0.1M $NaHCO_3$, pH 9.8 (see Current Protocols in Molecular Biology (1987), ed F. M. Ausubel, John Wiley & Sons, New York; pp. 10.8.1–10.8.6). Immunoblotting analysis showed that the nontransformed controls possessed nearly undetectable levels of PPO at this stage of leaf development. Five transgenic progeny showed prominent PPO immunostaining at ca. 59 kDa.

The five transgenic progeny and two nontransformed controls were then analyzed for PPO activity using methods described above (see Anal. Biochem. 77:486). PPO activity was not detected in leaves of nontransformed controls grown under these conditions. Three of the transgenic progeny (2-1C, 2-1E, 2-2E) had approximately equal levels of PPO activity: 95 mmol quinone formed/mg protein/min. The remaining two possessed PPO activity of 49 mmol quinone formed/mg protein/min (2-1A) and 177 mmol quinone formed/mg protein/min.

EXAMPLE V

Reduction of Potato Tuber PPO Via Antisense PPO Constructs

Following methods similar to those described in Examples III to IV, potato (*Solanum tuberosum* cv Van Gogh) were transformed with PPO in the antisense orientation using the CaMV 35S promoter. Regenerating plants were allowed to produce microtubers in tissue culture and then assayed for PPO. Based on preliminary microtuber PPO activity assays (catechol oxidase activity) of ca. 220 transformants, six were chosen for further study. Levels of tuber PPO activity in microtubers of control plants transformed with the vector only were 0.072 and 0.050 O.D./min; the nontransformed tubers possessed activity of 0.075 O.D./min. Of the seven transgenic tubers, 3 individuals (ST-7, ST-8, ST-10) possessed undetectable levels of PPO activity. ST-9, ST-5, ST-6 had activity of 0.004, 0.012, and 0.014 O.D./min, respectively.

Immunoblotting to determine level of the PPO polypeptide corresponded well with PPO activity. In all cases, the level of immunologically detectable PPO was lower in the transformants than in the nontransformed or vector-only transformant controls. PPO immunostaining was nearly undetectable for ST-7, ST-8, and slightly more abundant in ST-10. Immunostaining for PPO in tubers of ST-9 and ST-6 was very low; however, ST-5 showed a slightly higher amount of PPO.

Transformed plants were grown from tubers in the field. At the end of the growing season, the tubers were harvested and placed into cold storage. Tubers were then assayed for resistance to PPO- catalyzed melanization in an assay in which a standard amount of force was used to bruise each tuber. After a period of time each tuber was then inspected visually and rated for the extent of browning and discoloration in the region of the injury. Control tubers exhibited the expected levels of bruising and discoloration. All tubers possessing antisense constructs directing decreased PPO expression were rated as highly resistant to bruising (lacked extensive discoloration in the region around the site of injury).

EXAMPLE VI

More specifically to those examples above, potato leaf PPO cDNA pPPO-P1 was used to obtain two classes of PPO cDNA from a library constructed from mRNA of developing tubers (EMBO J. 8:23, 1989). The Class I clone from tuber (pKG45-8) is highly similar to the potato leaf pPPO-P1 (88.8% nucleotide sequence identity) (Plant Mol. Biol. 21:59, 1993), while the Class II clone (pKG59-4) is 77.6% identical to tomato PPO clones E and F (Plant Cell 4:135, 1992; Plant Mol. Biol. 21:1035, 1993). At least five different PPO genes or allelic variants of these genes are expressed in the potato tuber. The most abundant transcript in this tuber cDNA library belongs to the Class II gene family.

A series of antisense constructs were constructed that contained either full-length Class I or II tuber PPO genes, or 800 bp segments derived from the 5'- portions of both classes. The CaMV35S promoter, which gives high expression levels throughout the plant (Science 250:959, 1990), as well as two promoters which direct expression more specifically to the potato tuber: the granule bound starch synthase –G28 (GBSS) (J. Genet. and Breed. 44:311, 1990) and patatin type I (EMBO J. 9:23, 1989) were used as promoters. As a control, a construct was used in which the Class I PPO gene was inserted in a sense orientation regulated by the 35S CaMV promoter. Control constructs also consisted of vectors possessing the GUS marker gene (pBI121) (Plant Mol. Biol. Rep. 5:387, 1987).

The GBSS promoter was isolated from potato genomic DNA by PCR-aided cloning (Sambrook et al., 1989, Molecular cloning: a laboratory manual, Second Edition, Cold Spring Harbor Press) and contained DNA from nt –1184 to –8 (J. Genet. and Breed. 44:311, 1990). The sequence of this DNA fragment was determined to verify its identity with the published sequence. A HindIII site (5') and a BamHI site (3') were inserted at the termini by inclusion of the recognition sites in the PCR primers. This fragment was then inserted into the Ti-vector (pKG1001; described below) after treatment of both fragment and vector with HindIII and BamHI.

The Class I patatin promoter contained DNA from base –1514 to base –31 (Rosha-Sosa, M., et. al, EMBO J. 8:23–29 (1989). Restriction sites HindIII and BamHI were incorporated into the 5' and 3' ends using PCR to allow cloning into the Ti-vector, pKG1001, after treatment with HindIII and BamHI.

The CaMV 35S expression vector (pKG1001) was constructed from the vector PBl121 (Plant Mol. Biol. Rep. 5:387, 1987). The two tuber-specific promoters were then inserted into pKG1001 resulting in pKG1001/pat (containing the Class I patatin promoter) and pKG1001/GBSS containing the GBSS promoter. Antisense constructs were made, using each of the full-length PPO genes. Another set of constructs were made using the 800 bp region around the translation initiation site. Sections from Class I and Class II tuber PPOs were inserted into all three expression vectors described (pKG1001, pKG1001/pat and pKG1001/GBSS). One sense PPO gene construct was also made using the entire Class II cDNA in pKG1001. All potato PPO constructs were introduced into *Agrobacterium tumefaciens* strain GV3101 via electroporation and their integrity was confirmed by restriction enzyme analysis.

Using potato tissue explants (internodes) in co-cultivation experiments, 50 independent transformants were produced per construct and for each of two commercial tetraploid potato varieties, yielding 1400 transgenic lines. Potato plants (*Solanum tuberosum* cv. van Gogh and Diamant) were grown in vitro on MS medium (Physiol. Plant 15:473, 1962), supplemented with 30 g/l sucrose. Potato internode explants were transformed with *Agrobacterium tumefaciens* (strain GV 3101 (Nature 252:169, 1974) containing the antisense-PPO TI-plasmid constructs using co-cultivation methods essentially according to known protocols (Theor. Appl. Genet. 73:744, 1989).

In order to verify the transformation protocol and to obtain data on the average copy number of transgenes in the transformed lines, Southern blot analysis (Maniatis, T., et al., Molecular Cloning: A Laboratory Manual, Cold Spring Harbor Laboratory, Cold Spring Harbor, N.Y. 1982) was carried out at random on a sample of 50 lines including representatives from each construct type for both varieties chosen. All 50 putative transgenic lines so tested yielded the predicted restriction patterns, confirming successful transformation.

For an initial elimination screening of all 1400 transgenotes, the lines were cultured for micro-tuber production (Theor. Appl. Genet. 73:744, 1989), and micro-tuber tissues were used in a PPO enzyme assay (Plant Physiol. 81:614, 1986). 5 g fresh weight of micro-tubers from each line were homogenized in 5 ml 10 mM sodium acetate, pH 6. 50 mM catechol was used as substrate for PPO assay in a total volume of 1 ml, and replicate measures of enzyme activity were expressed as the rate of change of OD at 520 nm/ml extract/min at 25° C. Boiled extracts were tested and were shown to have no residual catecholase activity.

In the cultivars Diamant and van Gogh, 74% and 72% of antisense transformants, respectively, gave lower PPO enzyme activity than the nontransformed controls. In total, thirty-two lines harboring antisense PPO constructs had no detectable PPO activity. Only one of these lines was transformed with the patatin-promoter construct. Conversely, very high enzyme activity was found in individual lines expressing the PPO gene in the sense orientation. PPO enzyme activity in these transgenic plants reached levels up to 7-fold higher than transformed controls in Diamant, and up to 10-fold in van Gogh lines.

Both varieties showed reduced means in enzyme activity in all cases when either the CaMV 35S or GBSS promoters were used. In contrast, transgenic plants expressing antisense PPO genes from the patatin promoter constructs did not show statistically significant reductions. Although the reason for poor antisense inhibition of PPO activities in lines harbouring the patatin promoter constructs remains unclear, it is likely that the temporal expression pattern conferred on the introduced antisense PPO genes by the patatin promoter does not precisely coincide with the onset of endogenous PPO gene expression in the developing tuber.

There was no statistically significant differences between the ability of different antisense PPO genes (Class I and II) to suppress PPO activity, nor were there significant differences with respect to the size of the PPO segments used in the constructs.

Plant material for molecular analysis was taken from plants grown in 17 cm pots under greenhouse conditions. Poly-A+ RNA for Northern analysis was isolated from young leaves, from stolons initiating tuberisation with 3–5 mm swollen tips, and from 1–2 cm diameter tubers at the onset of flowering. To verify the data obtained from the enzyme assays and to obtain some understanding of the kinetics of PPO mRNA expression in the transgenic poatoes, total RNA was isolated (Plant Mol. Biol. 21:59, 1993) from young leaves, stolon tips initiating tuber formation, and young potato tubers. Poly-A+ RNA was extracted using poly-d[T] coupled to paramagnetic beads. 500 ng poly-A+ RNA was loaded per lane, electrophoretically separated RNA was capillary blotted onto Hybond N* membrane, and this was probed with an internal DNA fragment of the PPO cDNA pKG59-4 labeled with with $^{32}$p. The transgenics chosen for this experiment were nine van Gogh lines (three lines from every promoter combination) containing full length antisense PPO genes and showing the lowest PPO enzyme activity in micro-tubers. Constructs expressing the CaMV 35S-driven PPO gene in sense orientation and a CaMV 35S-GUS transformed control were also included. When poly-A+ RNA isolated from either leaf stolon or tubers of plants harboring the antisense CaMV 35S promoter PPO constructs was probed with an internal, double-stranded PPO cDNA probe, virtually no signal could be detected in any of the antisense lines tested. However, PPO transcript was detected in leaves of plants transformed with antisense constructs driven by both GBSS-G28 and patatin promoters. The weakly reduced transcript levels in leaves of the pGBSS/antisense PPO plants may well reflect the low level of GBSS promoter activity in these tissues.

It has been reported that expression of potato PPO is developmentally regulated; PPO mRNA can only be detected in early stages of organ development. The presence of endogenous PPO gene expression in stolons carrying the patatin antisense constructs may indicate that the patatin promoter may not become active in this tissue in time to prevent accumulation of PPO mRNA. The early expression of endogenous PPO genes during organogenesis, taken together with the long half-life of the PPO protein, may well allow enough PPO protein to be accumulated during tuber formation to give the high average enzyme activities in the patatin antisense lines as described above. In young tubers (1–2 cm diameter) some transcript is detected in one of the patatin lines. This is in accordance with the enzyme activity assays where this line also showed higher PPO enzyme activities in micro tubers. As expected, the sense PPO construct showed very high levels of PPO transcript in all tissues examined.

Protein was extracted from microtubers of the same lines as those used in the transcript analysis. Immunoblot analysis was carried out using a polyclonal antibody raised against purifed *Solanum berthaultii*. PPO protein extraction and immunoblotting was carried out (Plant Mol. Biol. 21:59). Protein was extracted from about 6 g of micro-tuber tissue of the transgenic lines used., and 10 ug of protein was loaded per lane. Tandem Coomassie blue-stained gels were run to verify equal loading. The results showed abundant PPO protein in the sense construct when compared to the GUS transformed control. Virtually no PPO protein could be detected in any lines carrying the CaMV 35S and GBSS constructs. However, control levels of PPO protein were revealed in the patatin-driven antisense PPO lines. These results are broadly in agreement with both the data from the enzyme assays and the mRNA analysis. The lack of PPO protein in one of the lines carrying CaMV 35S-antisense constructs and the complete lack of enzyme activity in microtubers of this line suggests that the transcript found in the Northerns may actually be due to an over abundance of antisense transcript rather than sense transcript from the endogenous gene.

In conventional potato breeding practice, standardized tests are carried out to determine the extent of discoloration after tuber bruising. Potatoes harvested from each transgenic line, grown in separate plots, were subjected to bruising under standard conditions: 2–3 kg of potatoes were placed in a shaking device comprised of a wooden box with padded walls. The box was mechanically agitated for 2 mins. After the bruising procedure, tubers were stored for 4 days at 8–10° C. Subsequently the potatoes were mechanically peeled until 80% of the skin was removed. The degree of browning is scored in terms of percent of the surface area affected by discoloration. The percentages are categorised into four classes and the number of tubers in each class are entered into the following formula, from which the BI is determined:

$$BI = \frac{100 \times (CI + 1) \times (CII + 2) \times (CIII + 3) \times (CIV + 4)}{6 \times (CI + CII + CIII + CIV)} \times 100$$

Wherein CI–CIV are the number of tubers categorised in a given class (CI; 0–0.2%, CII; 0.2–0.5%, CIII; 0.5–2.0% and CIV; >2% superficial browning). An index is calculated for blackspot sensitivity which takes into account the level of tuber discolouration after subjecting the tubers to standarized mechanical damage and subsequent storage at low temperature. The resulting Browning Index (BI) ranges from 0 to 50. BI's from tubers of 50 lines were determined after in vitro propagation and planting in field trials. Lines were selected on the basis of enzyme assays described above. A significantly lower level of discolouration was noted on visual scoring, after tubers had been peeled, in lines carrying either CaMV 35S or GBSS promoter driven antisense PPO genes. These results were further substantiated in the BI results, where significantly lower indexes were calculated in these transformants for both varieties when compared to the patatin promoter constructs even though the latter had also been preselected on the basis of low enzyme levels.

The conclusion that can be drawn from these tests is that a high percentage of blackspot bruising-resistant lines can be selected from transgenic potatoes expressing an antisense PPO-gene under the control of CaMV 35S or GBSS promoters. These results are in stark contrast with previous attempts to select blackspot resistance from tissue culture-derived somaclonal variant potato lines, an approach which has proven unsuccessful. In addition, transformation of potato with PPO in a sense orientation is sufficient to generate plants which express PPO at levels up to 10 times that of nontransformed plants.

EXAMPLE VII (Tomato anti-sense)

A 2 kb potato PPO cDNA (PPO-P1) from immature leaves was blunt end ligated in the reverse orientation into the *Agrobacterium tumefaciens* binary transformation vector pBl121 under the regulation of the CAMV 35S promoter and the nos terminator. The pBl121 vector was restriction enzyme digested with Sma I and Sst I, incubated with T4 DNA polymerase and the vector backbone was gel purified essentially as described (Maniatis, T., et al., Molecular Cloning: A Laboratory Manual, Second Edition, Cold Spring Harbor Laboratory, Cold Spring Harbor, N.Y. 1989). A 2 kb potato PPO cDNA (PPO-P1) from immature leaves (see Plant Mol. Biol. 21: 59, 1993) cloned in pBluescript (Stratagene), restriction digested with Sma I and Xho I to liberate the PPO cDNA from the vector, incubated with the Klenow fragment of DNA polymerase I and gel purified. Products of two independent blunt-end ligation events were electroporated into *Agrobacterium tumefaciens* strain LBA4404 and used to transform tomato explants as described below.

*Agrobacterium tumefaciens* strain LBA 4404 containing the construct of interest was streaked from a glycerol stock onto selective LB medium (50 mg/L kanamycin) and incubated for 3 days at 30° C. One day prior to incubating the conditioned tomato explants with *A. tumefaciens*, selective LB medium was inoculated with several colonies and cultured with shaking at 30° C. until an $OD_{600}$ of between 0.3 and 1.0 was reached. The culture was centrifuged for 5 minutes 6,000×g and the pellet was resuspended in MS-0.2% to obtain a final $OD_{600}$ of 0.3.

The tomato transformation protocol was based upon known methods (Biotechnology 5:726, 1987). *Lycopersicon esculentum* cv. Moneymaker seeds were germinated on ½ MSO (half-strength) medium (Physiol Plant 15:473, 1962) at 25° C. with a 16:8 hour light:dark photoperiod; major and minor salts, 0.06 mM ethylenediamine tetraacetic acid ferric sodium salt (EDFS), 2 g/l thiamine HCl, 50 mg/l myo-inositol, 0.5 mg/l pyridoxine HCl, 0.5 mg/l nicotinic acid, 1% (w/v) sucrose, 0.8% (w/v) agar, pH 5.8. Before the first true leaf was evident (ca. 5 days), cotyledons were excised and cut into three pieces. Hypocotyls were excised just below the apical meristem and cut into two 6 mm long cross-sections. Explants were placed on TR medium (major and minor salts, 0.12 mM EDFS, 100 mg/l myo-inositol, 10 mg/l thiamine HCl, 1 mg/l nicotinic acid, 1 mg/l pyridoxine HCl, 1 mg/l zeatin, 0.1 mg/l indole-3-acetic acid (IAA), 3% (w/v) sucrose, 0.8% (w/v) agar at pH 5.8) utilizing a tobacco suspension feeder layer and incubated for two days.

Explants were incubated in a 1/10 dilution of the Agrobacterium culture prepared as described above for 10 minutes with gentle shaking and returned to the TR plates. After four days of cocultivation, explants were transferred to TRS medium [TR medium with 50 mg/l kanamycin and 400 mg/l timentin]. Shoots regenerated within 2 to 4 weeks, were excised and placed in P-medium supplemented with 0.18 mg/l IAA, 50 mg/l kanamycin and 400 mg/l timentin. Plants that formed roots on the selective P-medium were transferred to soil.

Transformed controls consisted of plants transformed as above with pBI121 possessing the reporter gene GUS (β-glucuronidase), and nontransformed controls were tissue culture-regenerated plants. Genomic DNA isolated from kanamycin-resistant putative transformants was restriction digested with EcoRI and DNA blot analyzed using an Npt II probe. The number of T-DNA integrations ranged from 1 to 3 copies. DNA blot analysis of initial putative kanamycin-resistant transformants revealed an escape rate of less than 5%. Therefore, the majority of the plants regenerating on kanamycin-containing medium were transformed with the T-DNA.

A total of 34 independent R0 antisense transformants were regenerated. Five of these plants exhibited leaf PPO activity levels 30% or less of wild type. Gel electrophoresis, electroblotting and immunoblotting procedures were performed as described (Plant Mol. Biol. 21, 59, 1993). Tomato tissues and organs were frozen in liquid nitrogen, homogenized in extraction buffer (0.1M Tris-HCl pH 7, 3% (v/v) polyvinylpolypyrrolidone, 0.1M KCl, 1 mM phenylmethylsulfonylfluoride, 1 ug/ml leupeptin, 5 ug/ml chymostatin, 1% (v/v) Triton X-100, 1 mM NaEDTA), and centrifuged at 9600×g for 20 minutes at 4° C. Supernatants were recovered and quantified by the method of Bradford (Anal Biochem 72, 248, 1976). To verify equal loading of protein extracts, parallel coomassie-stained gels were prepared. PPO activity assays were performed on the protein extracts (Analytical Biochem 77:486, 1977). Catalase (84 units/ul) was routinely added to each sample to eliminate peroxidase activity, thus providing differentiation of polyphenol oxidase activity and peroxidase activity. Peroxidase assays performed on the same protein extracts reveal no significant difference in peroxidase levels for nontransformed control, GUS control and antisense plants. Laccase activity is absent in leaf extracts of this tomato cultivar. Immunoblots of these transformants show a consistent correlation between the intensity of PPO signal and PPO activity determined from whole leaf protein extracts.

Of the five $R_0$ plants, one (plant A1-4) possessed no detectable PPO activity in any tissue or organ analyzed and was further characterized. Total RNA was isolated and 25 ug was analyzed (Plant Mol. Biol. 21:59, 1993). PPO-P1 was used as the PPO probe and a soybean actin genomic fragment was used to verify equal loading of RNAs. Both were $^{32}$P-labeled as described above. To determine if the antisense phenotype observed in the R0 generation of this plant was stable, the plant was selfed and the R1 generation was analyzed. Conventional DNA blotting [Plant Mol. Biol. 21:1035, 1993; except the gel was blotted onto Hybond-N+ (Amersham) and probed with a random hexamer (Boehringer Manheim) $^{32}$P-labeled Npt II-2 kb fragment gel purified from a Pst I digest of pBl121] was conducted. Tomato genomic DNA was isolated, and DNA blot analysis of 17 selfed progeny (R1 generation) of A1-4 revealed a 3:1 transformed:nontransformed segregation ratio indicating that the two T-DNA copies stably segregate as a single locus.

Two R1 progeny (A1-4-1 and A1-4-3) did not possess the transgenic locus, and exhibited PPO activity and immunoblot profile similar to nontransformed control plants (NT-2). Conversely, the other R1 progeny which were either heterozygous (A1-4,-1-5, 1-7, 1-11, 1-13, 1-14, 1-16, 1-17) or homozygous (A1-4-4, -16, -18) for the presence of the transgenic locus, based on DNA blot analysis did not exhibit PPO protein or activity. These analyses demonstrate that the PPO antisense biochemical phenotype co-segregates with the presence of the transgenic locus. One of the four homozygous transgenic progeny, A1-4-6, was selfed to obtain R2 progeny, of which all possessed the antisense transgene as determined by DNA blot analysis. RNA blot analysis (using PPO-P1 as a probe) of leaves and flowers from nontransformed control NT-2A and 1-4-6 showed PPO mRNA as a 2 kb band in node 1 leaves and flowers of the nontransformed control, but absent in leaves and flowers of A1-4-6.

The PPO null phenotype (defined by lack of PPO activity, absence of immunologically detectable PPO protein, and absence of PPO mRNA in leaves and flowers) was stable over at least three generations and produced no apparent deleterious effects on plant growth and vigor under greenhouse conditions.

EXAMPLE VIII

Tomato Sense and Effect of Modified PPO Expression on Insect Herbivores

Plants overexpressing PPO may also be generated by transformation in a sense orientation with a full-length PPO cDNA, for example from tomato corresponding to PPO B in the sense orientation under the control of the 35S promoter and nos terminator in pBI121 and using cloning strategies and analyses similar to those described in Example VII. In this Example, R0 plants were confirmed as transformed by DNA blotting. Immunoblotting (Plant Mol. Biol. 21:59, 1993). PPO activity assay identified 4 plants with PPO activity levels 4 to 5 times higher than control plants.

To demonstrate the effect of modified PPO expression on insect herbivore pests, *Leptinotarsa decemlineata* (Colorado potato beetle) egg masses were obtained from a colony maintained on tomato. Egg masses were incubated at 27° C. on wet Whatman paper in a growth chamber with 50 percent relative humidity and a 16:8 hour light:dark photoperiod. Eggs hatched 5 days after oviposition and the neonate larvae were allowed to disperse from the egg masses. Leaf discs were obtained from node 3–5 leaves of nontransformed control, antisense PPO, or sense PPO overexpressing tomato plants. Each treatment consisted of six cohorts of twelve larvae (72 total larvae per treatment) and were arranged in a randomized design throughout the experiment. At the first instar, two larvae were placed in one well of a 12 well culture plate which contained one leaf disc. From the second instar onwards, larvae were individualized. From the third instar onwards, individualized larvae were placed in six well tissue culture plates. A piece of moist Whatman paper was placed in each well to maintain adequate humidity and wetted at needed. Fresh leaf material and Whatman paper were provided every 48 hours up to the third instar and every 24 hours thereafter. Cohort larvae were weighed as a group every two days. Mortality and instar stage were recorded daily.

After 8 days, mortality was 45, 68 and 79%, respectively for Colorado potato beetle reared on antisense PPO, control, and PPO sense overexpression plants, respectively. The number of Colorado potato beetle larvae surviving to the fourth instar stage by day 8 was 25, 9, and 5 for antisense PPO, control, and PPO sense overexpression plants, respectively. The mean weight of fourth instar larve at day 8 was 43, 32 and 24 mg for Colorado potato beetle larvae reared on antisense PPO, control, and PPO sense overexpression plants, respectively.

Clearly, modification of PPO expression results in significant effects on growth and development of an important insect pest, the Colorado potato beetle. We believe it is a reasonable expectation that PPO sense overexpression will have similarly negative effects on other insect pests and the example presented here with Colorado potato beetle in no way limits the scope of this invention to this specific pest, nor to the modification of PPO exclusively in this crop plant.

The cloning of tomato and potato PPO cDNAs, according to the present invention, provides a unique opportunity to investigate what have previously been the most intractable questions regarding PPO. As a result of the present invention, it is now possible to address the function and expression of PPOs by using transgenic plants over-and under-expressing PPO. Transgenic plants with altered PPO expression can be used to alter the economic impacts of PPO on the postharvest physiology of food plants, and are similarly important in efforts to exploit PPO to increase the pest tolerance of crop plants.

The ability to alter PPO levels in commercially important plants will achieve both an increase in the pest tolerance of plants and a decrease in the deleterious effect of PPO on crop quality. With an increased PPO level in foliage (or other non-food components) of crop plants providing an increase in pest tolerance, the present invention could have general use for providing protection from pests in a number of valuable commercial crops. Alternatively, by providing a means for selective down-regulation of PPO expression in various plant organs, the present invention could decrease the economic impact of an array of PPO- catalyzed brownin syndromes and eliminate or reduce the need for antioxidant additives to preserve and/or process these commodities.

The sequence listing for the amino acid and nucleic acid sequences described herein is as follows:

I claim:

1. An isolated nucleic acid molecule encoding a plant polyphenol oxidase.

2. The isolated nucleic acid molecule of claim 1 wherein said nucleic acid is deoxyribonucleic acid.

3. The isolated nucleic acid molecule of claim 2 wherein said deoxyribonucleic acid is cDNA.

4. The isolated nucleic acid molecule of claim 3 wherein said cDNA has a nucleotide sequence as shown in SEQ ID NO:1.

5. The isolated nucleic acid molecule of claim 3 wherein said cDNA has a nucleotide sequence as shown in SEQ ID NO:5.

6. The isolated nucleic acid molecule of claim 3 wherein said cDNA has a nucleotide sequence as shown in SEQ ID NO:14.

7. The isolated nucleic acid molecule of claim 3 wherein said cDNA has a nucleotide sequence as shown in SEQ ID NO:17.

8. The isolated nucleic acid molecule of claim 1 wherein said plant polyphenol oxidase is a tomato polyphenol oxidase.

9. The isolated nucleic acid molecule of claim 1 wherein said plant polyphenol oxidase is a potato polyphenol oxidase.

10. The isolated nucleic acid molecule of claim 1 wherein said nucleic acid molecule encodes an amino acid sequence as shown in SEQ ID NO:4.

11. The isolated nucleic acid molecule of claim 1 wherein said nucleic acid molecule encodes an amino acid sequence as shown in SEQ ID NO:8.

12. The isolated nucleic acid molecule of claim 1 wherein said nucleic acid molecule encodes an amino acid sequence as shown in SEQ ID NO:16.

13. The isolated nucleic acid molecule of claim 1 wherein said nucleic acid molecule encodes an amino acid sequence as shown in SEQ ID NO:19.

14. The isolated nucleic acid molecule of claim 1 wherein said nucleic acid is ribonucleic acid.

15. The isolated nucleic acid molecule of claim 14 wherein said ribonucleic acid is mRNA.

16. An isolated antisense nucleic acid molecule complementary to the mRNA of claim 15.

17. The isolated antisense nucleic acid molecule of claim 16 wherein said nucleic acid comprises ribonucleic acid.

18. The isolated antisense nucleic acid molecule of claim 16 wherein said nucleic acid comprises single-stranded deoxyribonucleic acid.

19. The isolated antisense nucleic acid molecule of claim 16 wherein said plant polyphenol oxidase is a tomato polyphenol oxidase.

20. The isolated antisense nucleic acid molecule of claim 16 wherein said plant polyphenol oxidase is a potato polyphenol oxidase.

21. A recombinant cell transformed with the isolated antisense nucleic acid molecule of claim 16.

22. The recombinant cell of claim 21 wherein said recombinant cell is *Agrobacterium tumefaciens*.

23. An expression vector comprising the isolated antisense nucleic acid molecule of claim 16.

24. The expression vector of claim 23 wherein said expression vector is a plasmid.

25. A cell comprising the expression vector of claim 23.

26. The cell of claim 25 wherein said cell is *Agrobacterium tumefaciens*.

27. A transgenic plant transformed with the isolated antisense nucleic acid molecule of claim 16.

28. The transgenic plant of claim 27 wherein said plant is a tomato plant.

29. The transgenic plant of claim 27 wherein said plant is a potato plant.

30. The transgenic plant of claim 27 wherein said plant is a tobacco plant.

31. A method of decreasing polyphenol oxidase production in a plant, said method comprising:
   selecting a plant with a first level of polyphenol oxidase production; and
   introducing the isolated antisense nucleic acid molecule of claim 16 into said plant, wherein said isolated antisense nucleic acid molecule blocks translation of said mRNA so as to decrease expression of polyphenol oxidase, resulting in a second level of polyphenol oxidase production in said plant, said second level being less than said first level.

32. The method of claim 31 wherein said second level is about zero.

33. The method of claim 31 wherein said plant is a tomato plant.

34. The method of claim 31 wherein said plant is a potato plant.

35. The method of claim 31 wherein said plant is a tobacco plant.

36. A recombinant cell transformed with the isolated nucleic acid molecule of claim 1.

37. The recombinant cell of claim 36 wherein said recombinant cell is *Agrobacterium tumefaciens*.

38. An expression vector comprising the isolated nucleic acid molecule of claim 1.

39. The expression vector of claim 38 wherein said expression vector is a plasmid.

40. A cell comprising the expression vector of claim 38.

41. The cell of claim 40 wherein said cell is *Agrobacterium tumefaciens*.

42. A transgenic plant transformed with the isolated nucleic acid molecule of claim 1.

43. The transgenic plant of claim 42 wherein said plant is a tomato plant.

44. The transgenic plant of claim 42 wherein said plant is a potato plant.

45. The transgenic plant of claim 42 wherein said plant is a tobacco plant.

46. A method of increasing polyphenol oxidase production in a plant, said method comprising:

selecting a plant with a first level of polyphenol oxidase production; and introducing the nucleic acid molecule of claim 1 into said plant, wherein when said nucleic acid molecule is expressed and polyphenol oxidase is produced, resulting in a second level of polyphenol oxidase production in said plant, said second level being greater than said first level.

47. The method of claim 46 wherein said first level is about zero.

48. The method of claim 46 wherein said plant is a tomato plant.

49. The method of claim 46 wherein said plant is a potato plant.

50. The method of claim 46 wherein said plant is a tobacco plant.

51. A method of obtaining DNA encoding a plant polyphenol oxidase, said method comprising:

selecting a DNA molecule encoding a plant polyphenol oxidase, said DNA molecule having a nucleotide sequence selected from the group consisting of SEQ ID NO:1, SEQ ID NO:5, SEQ ID NO:14, and SEQ ID NO:17;

designing an oligonucleotide probe for a plant polyphenol oxidase based on the nucleotide sequence of the selected DNA molecule;

probing a genomic or cDNA library of a plant with the oligonucleotide probe; and obtaining clones from said library that are recognized by said oligonucleotide probe, so as to obtain DNA encoding a plant polyphenol oxidase.

\* \* \* \* \*